US012569319B2

(12) United States Patent
Fridman

(10) Patent No.: US 12,569,319 B2
(45) Date of Patent: Mar. 10, 2026

(54) COMBINED FACE SCANNING AND INTRAORAL SCANNING

(71) Applicant: Align Technology, Inc., San Jose, CA (US)

(72) Inventor: Edi Fridman, Rishon le Zion (IL)

(73) Assignee: Align Technology, Inc., San Jose, CA (US)

( * ) Notice: Subject to any disclaimer, the term of this patent is extended or adjusted under 35 U.S.C. 154(b) by 214 days.

(21) Appl. No.: 18/355,300

(22) Filed: Jul. 19, 2023

(65) Prior Publication Data

US 2024/0024076 A1      Jan. 25, 2024

Related U.S. Application Data

(60) Provisional application No. 63/391,654, filed on Jul. 22, 2022.

(51) Int. Cl.
| | |
|---|---|
| *A61C 7/00* | (2006.01) |
| *A61C 9/00* | (2006.01) |
| *A61C 13/34* | (2006.01) |
| *G06T 5/80* | (2024.01) |
| *G06T 7/33* | (2017.01) |
| *G06T 19/20* | (2011.01) |
| *G16H 30/20* | (2018.01) |
| *G16H 50/50* | (2018.01) |

(52) U.S. Cl.
CPC ............ *A61C 7/002* (2013.01); *A61C 9/0053* (2013.01); *A61C 13/34* (2013.01); *G06T 5/80* (2024.01); *G06T 7/344* (2017.01); *G06T 19/20* (2013.01); *G16H 30/20* (2018.01); *G16H 50/50* (2018.01); *G06T 2200/04* (2013.01); *G06T 2207/30036* (2013.01); *G06T 2210/41* (2013.01); *G06T 2219/2004* (2013.01); *G06T 2219/2021* (2013.01)

(58) Field of Classification Search
None
See application file for complete search history.

(56) References Cited

U.S. PATENT DOCUMENTS

| | | | |
|---|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |

(Continued)

*Primary Examiner* — Miya J Cato
(74) *Attorney, Agent, or Firm* — Lowenstein Sandler LLP

(57) ABSTRACT

A system comprises an intraoral scanner, a three-dimensional (3D) image capture device, and a computing device operatively coupled to the intraoral scanner and to the 3D image capture device. The computing device receives intraoral scan data of a dental site of a patient generated by the intraoral scanner during intraoral scanning. The computing device further receives one or more 3D images of a face of the patient generated by the 3D image capture device during the intraoral scanning, wherein the intraoral scanner is captured in the one or more 3D images. The computing device registers the one or more 3D images of the face of the patient to the first intraoral scan data based at least in part on a first position of the intraoral scanner relative to the face of the patient in the one or more 3D images.

20 Claims, 10 Drawing Sheets

(56) References Cited

U.S. PATENT DOCUMENTS

| | | | |
|---|---|---|---|
| 6,697,164 B1 | 2/2004 | Babayoff et al. | |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Ampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 * | 9/2016 | Kopelman | G06T 17/00 |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,813,727 B2 | 10/2020 | Sabina et al. | |
| 10,839,481 B1 * | 11/2020 | Chen | G06T 7/344 |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 11,013,581 B2 | 5/2021 | Sabina et al. | |
| D925,739 S | 7/2021 | Shalev et al. | |
| 11,096,765 B2 | 8/2021 | Atiya et al. | |
| 11,238,586 B2 | 2/2022 | Minchenkov et al. | |
| 11,367,192 B2 | 6/2022 | Kopelman et al. | |
| 11,455,727 B2 | 9/2022 | Minchenkov et al. | |
| 11,478,132 B2 | 10/2022 | Kopelman et al. | |
| 11,563,929 B2 | 1/2023 | Saphier et al. | |
| 11,633,268 B2 | 4/2023 | Moalem et al. | |
| 11,707,238 B2 | 7/2023 | Moshe et al. | |
| RE49,605 E | 8/2023 | Kopelman | |
| 2014/0120493 A1 * | 5/2014 | Levin | G06T 5/73 |
| | | | 433/29 |
| 2019/0388193 A1 | 12/2019 | Saphier et al. | |
| 2020/0281702 A1 | 9/2020 | Kopelman et al. | |
| 2021/0030503 A1 | 2/2021 | Shalev et al. | |
| 2021/0059796 A1 | 3/2021 | Weiss et al. | |
| 2021/0121049 A1 | 4/2021 | Rudnitsky et al. | |
| 2021/0128281 A1 | 5/2021 | Peleg | |
| 2021/0137653 A1 | 5/2021 | Saphier et al. | |
| 2021/0196152 A1 | 7/2021 | Saphier et al. | |
| 2022/0160431 A1 * | 5/2022 | Mozes | A61B 6/032 |
| 2024/0033061 A1 * | 2/2024 | Hultgren | A61C 13/0004 |
| 2024/0189065 A1 * | 6/2024 | Schnabel | A61C 9/004 |
| 2024/0261068 A1 * | 8/2024 | Ciriello | H04N 23/685 |
| 2024/0382288 A1 * | 11/2024 | Jaisson | G16H 20/40 |

* cited by examiner

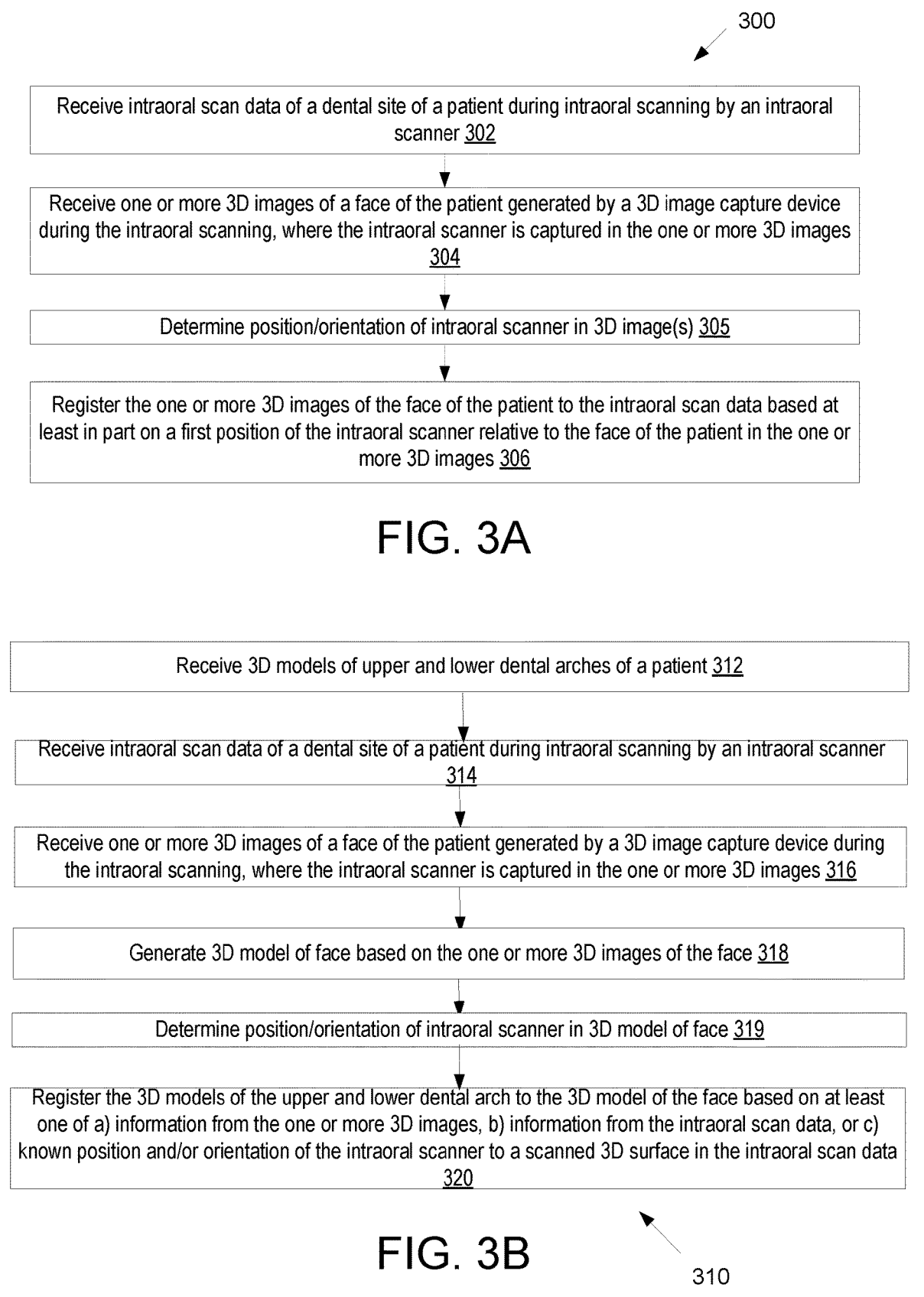

300

| Receive intraoral scan data of a dental site of a patient during intraoral scanning by an intraoral scanner 302 |

▼

| Receive one or more 3D images of a face of the patient generated by a 3D image capture device during the intraoral scanning, where the intraoral scanner is captured in the one or more 3D images 304 |

▼

| Determine position/orientation of intraoral scanner in 3D image(s) 305 |

▼

| Register the one or more 3D images of the face of the patient to the intraoral scan data based at least in part on a first position of the intraoral scanner relative to the face of the patient in the one or more 3D images 306 |

FIG. 3A

| Receive 3D models of upper and lower dental arches of a patient 312 |

▼

| Receive intraoral scan data of a dental site of a patient during intraoral scanning by an intraoral scanner 314 |

▼

| Receive one or more 3D images of a face of the patient generated by a 3D image capture device during the intraoral scanning, where the intraoral scanner is captured in the one or more 3D images 316 |

▼

| Generate 3D model of face based on the one or more 3D images of the face 318 |

▼

| Determine position/orientation of intraoral scanner in 3D model of face 319 |

▼

| Register the 3D models of the upper and lower dental arch to the 3D model of the face based on at least one of a) information from the one or more 3D images, b) information from the intraoral scan data, or c) known position and/or orientation of the intraoral scanner to a scanned 3D surface in the intraoral scan data 320 |

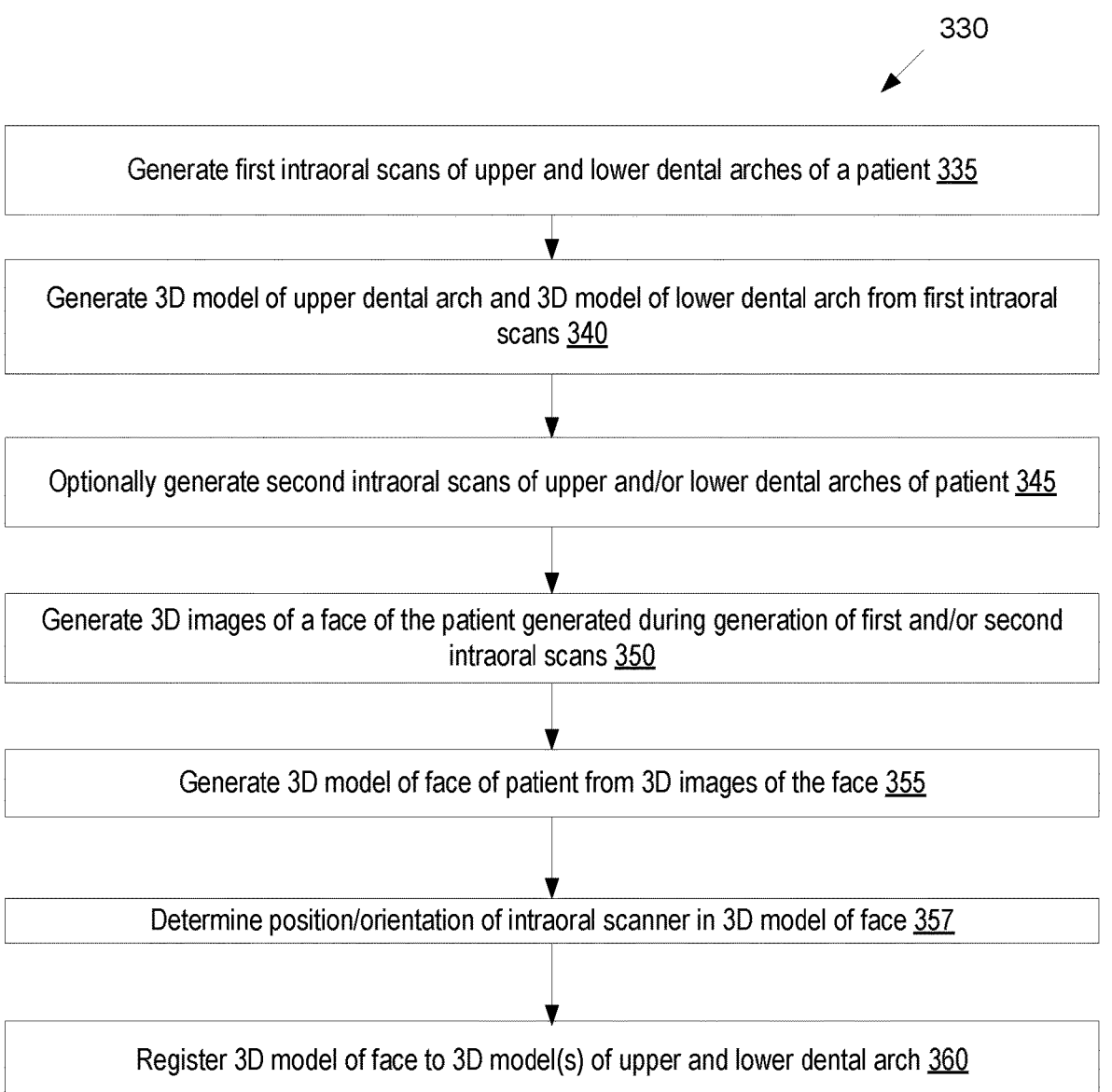

330

Generate first intraoral scans of upper and lower dental arches of a patient 335

Generate 3D model of upper dental arch and 3D model of lower dental arch from first intraoral scans 340

Optionally generate second intraoral scans of upper and/or lower dental arches of patient 345

Generate 3D images of a face of the patient generated during generation of first and/or second intraoral scans 350

Generate 3D model of face of patient from 3D images of the face 355

Determine position/orientation of intraoral scanner in 3D model of face 357

Register 3D model of face to 3D model(s) of upper and lower dental arch 360

FIG. 3C

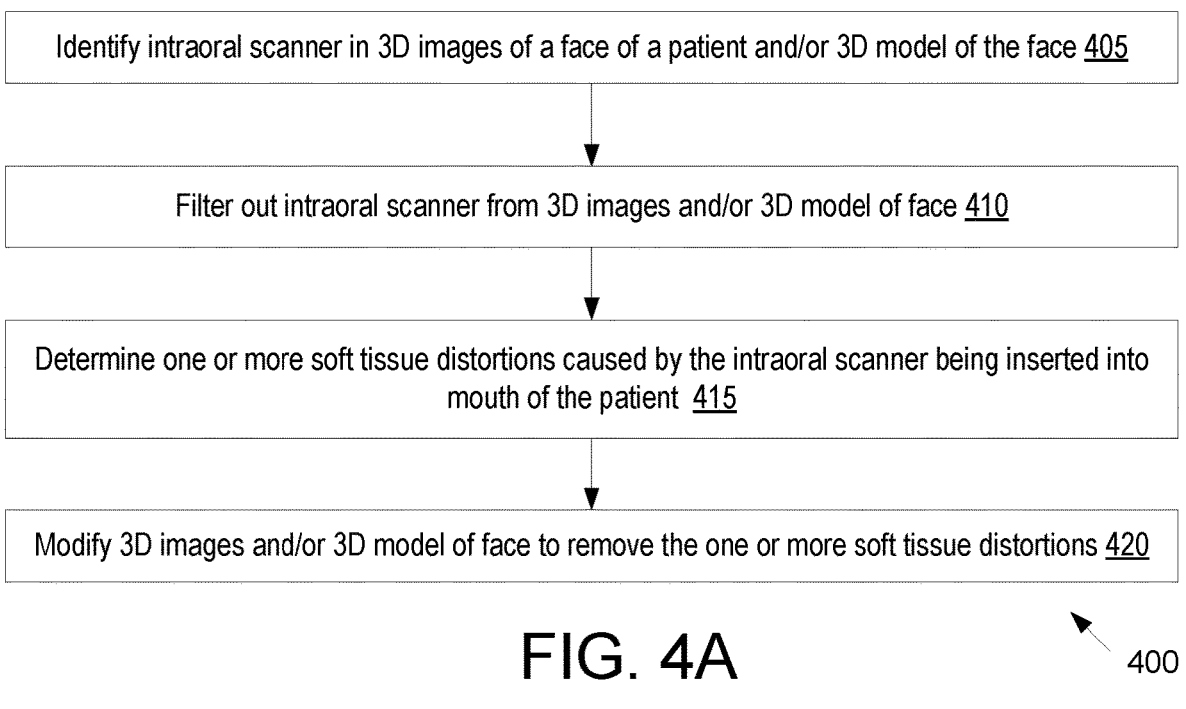

Identify intraoral scanner in 3D images of a face of a patient and/or 3D model of the face 405

Filter out intraoral scanner from 3D images and/or 3D model of face 410

Determine one or more soft tissue distortions caused by the intraoral scanner being inserted into mouth of the patient 415

Modify 3D images and/or 3D model of face to remove the one or more soft tissue distortions 420

FIG. 4A     400

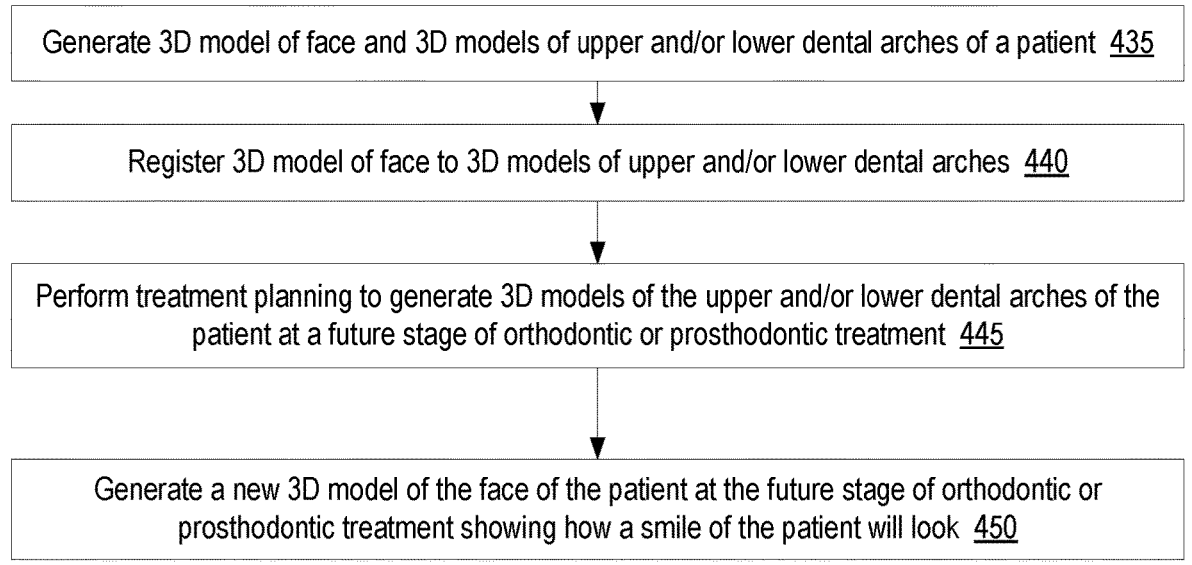

Generate 3D model of face and 3D models of upper and/or lower dental arches of a patient 435

Register 3D model of face to 3D models of upper and/or lower dental arches 440

Perform treatment planning to generate 3D models of the upper and/or lower dental arches of the patient at a future stage of orthodontic or prosthodontic treatment 445

Generate a new 3D model of the face of the patient at the future stage of orthodontic or prosthodontic treatment showing how a smile of the patient will look 450

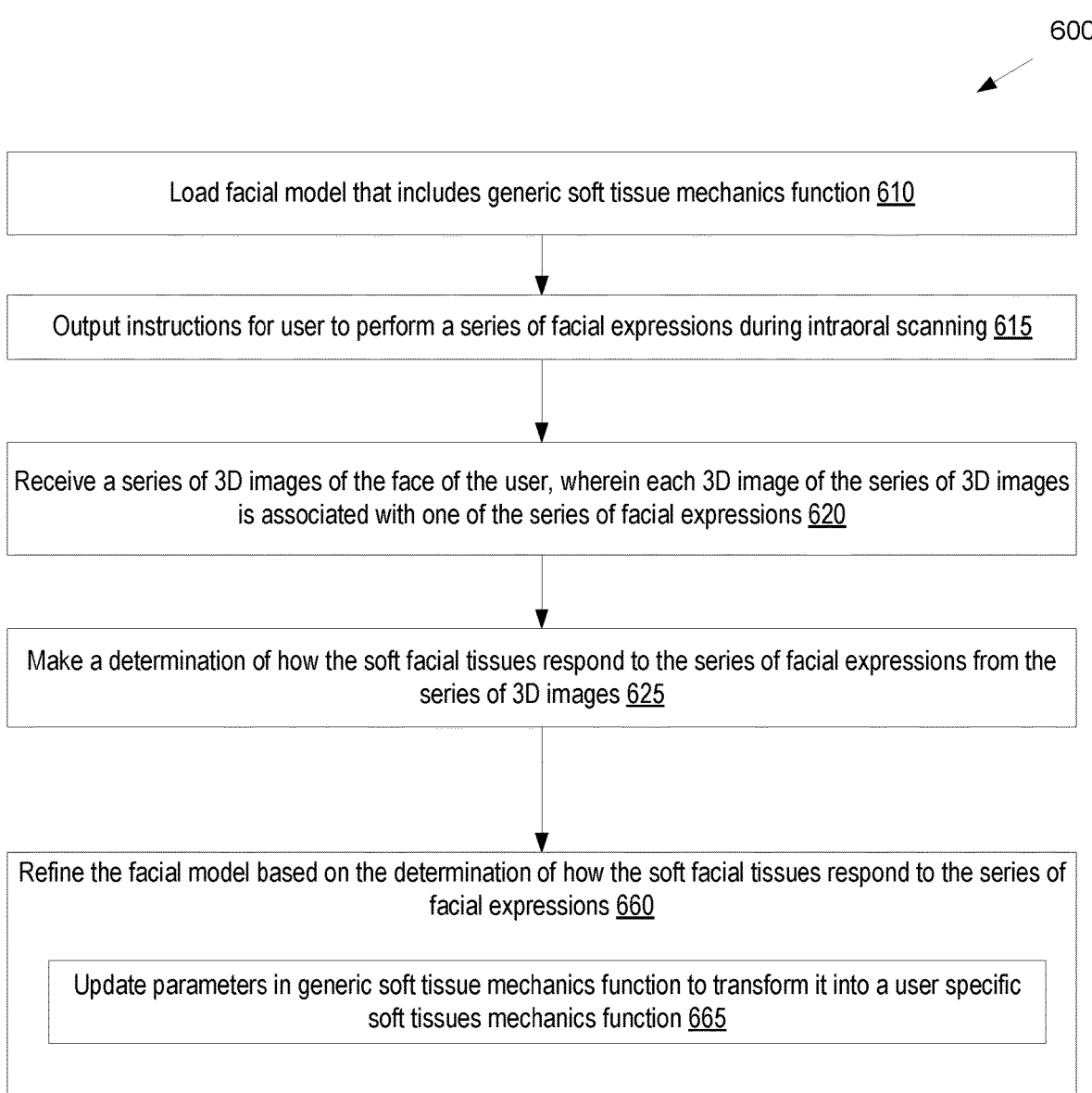

Load facial model that includes generic soft tissue mechanics function 610

Output instructions for user to perform a series of facial expressions during intraoral scanning 615

Receive a series of 3D images of the face of the user, wherein each 3D image of the series of 3D images is associated with one of the series of facial expressions 620

Make a determination of how the soft facial tissues respond to the series of facial expressions from the series of 3D images 625

Refine the facial model based on the determination of how the soft facial tissues respond to the series of facial expressions 660

Update parameters in generic soft tissue mechanics function to transform it into a user specific soft tissues mechanics function 665

FIG. 6

COMBINED FACE SCANNING AND INTRAORAL SCANNING

RELATED APPLICATIONS

This patent application claims the benefit under 35 U.S.C. § 119(e) of U.S. Provisional Application No. 63/391,654, filed Jul. 22, 2022, which is incorporated by reference herein.

TECHNICAL FIELD

Embodiments of the present disclosure relate to the field of dentistry and, in particular, to combined face scanning and intraoral scanning.

BACKGROUND

Many general practice dentists and orthodontists use an intraoral scanner to generate 3D models of their patient's dental arches. However, such 3D models of patient dental arches are not generally combined with facial models of patient faces.

SUMMARY

In a $1^{st}$ implementation, a system comprises: an intraoral scanner; a three-dimensional (3D) image capture device; and a computing device operatively coupled to the intraoral scanner and to the 3D image capture device, the computing device to: receive first intraoral scan data of a dental site of a patient generated by the intraoral scanner during intraoral scanning; receive one or more 3D images of a face of the patient generated by the 3D image capture device during the intraoral scanning, wherein the intraoral scanner is captured in the one or more 3D images; and register the one or more 3D images of the face of the patient to the first intraoral scan data based at least in part on a first position of the intraoral scanner relative to the face of the patient in the one or more 3D images.

A $2^{nd}$ implementation may further extend the $1^{st}$ implementation. In the $2^{nd}$ implementation, the one or more 3D images of the face of the patient are registered to the first intraoral scan data based further on a known second position of the intraoral scanner relative to a 3D surface in the first intraoral scan data generated by the intraoral scanner.

A $3^{rd}$ implementation may further extend the $1^{st}$ or $2^{nd}$ implementation. In the $3^{rd}$ implementation, the one or more 3D images of the face of the patient are registered to the first intraoral scan data based further on a first orientation of the intraoral scanner relative to the face of the patient in the one or more 3D images and a known second orientation of the intraoral scanner relative to the 3D surface in the first intraoral scan data generated by the intraoral scanner.

A $4^{th}$ implementation may further extend any of the $1^{th}$ rough $3^{rd}$ implementations. In the $4^{th}$ implementation, the computing device is further to generate a 3D model of at least one of face of the patient or the dental site using the one or more 3D images of the face of the patient and the first intraoral scan data of the dental site of the patient.

A $5^{th}$ implementation may further extend any of the $1^{th}$ rough $4^{th}$ implementations. In the $5^{th}$ implementation, the computing device is further to: receive a first 3D model of an upper dental arch of the patient and a second 3D model of a lower dental arch of the patient; generate a third 3D model of the face of the patient based on the one or more 3D images; and register at least one of the first 3D model of the upper dental arch or the second 3D model of the lower dental arch to the third 3D model of the face based at least in part on the first position of the intraoral scanner relative to the face of the patient in the one or more 3D images.

A $6^{th}$ implementation may further extend the $5^{th}$ implementation. In the $6^{th}$ implementation, the computing device is further to: receive second intraoral scan data of the upper dental arch and third intraoral scan data of the lower dental arch; generate the first 3D model of the upper dental arch based on the second intraoral scan data; and generate the second 3D model of the lower dental arch based on the third intraoral scan data.

A $7^{th}$ implementation may further extend the $5^{th}$ or $6^{th}$ implementation. In the $7^{th}$ implementation, the computing device is further to: receive second intraoral scan data of the dental site of the patient during the intraoral scanning; receive one or more additional 3D images of the face of the patient during the intraoral scanning, wherein the intraoral scanner is captured in the one or more additional 3D images, and wherein a position of the lower dental arch relative to the upper dental arch is different in the one or more additional 3D images than in the one or more 3D images; generate a fourth 3D model of the face of the patient based on the one or more additional 3D images; and register at least one of the first 3D model of the upper dental arch or the second 3D model of the lower dental arch to the fourth 3D model of the face based at least in part on a second position of the intraoral scanner relative to the face of the patient in the one or more additional 3D images.

An $8^{th}$ implementation may further extend the $5^{th}$ rough $7^{th}$ implementations. In the $8^{th}$ implementation, the computing device is further to filter out the intraoral scanner from at least one of the one or more 3D images of the face or the third 3D model of the face.

A $9^{th}$ implementation may further extend the $5^{th}$ rough $8^{th}$ implementations. In the $9^{th}$ implementation, the computing device is further to: determine one or more soft tissue distortions caused by the intraoral scanner being inserted into a mouth of the patient; and modify at least one of the one or more 3D images of the face or the third 3D model of the face to remove the one or more soft tissue distortions.

An $10^{th}$ implementation may further extend the $5^{th}$ rough $9^{th}$ implementations. In the $10^{th}$ implementation, the computing device is further to: perform treatment planning to generate a fourth 3D model of the upper dental arch at a future stage of orthodontic or prosthodontic treatment and a fifth 3D model of the lower dental arch at the future stage of orthodontic or prosthodontic treatment; and generate a sixth 3D model of the face of the patient at the future stage of orthodontic or prosthodontic treatment showing how a smile of the patient will look at the future stage of orthodontic or prosthodontic treatment.

In an $11^{th}$ implementation, a method comprises: receiving first intraoral scan data of a dental site of a patient during intraoral scanning by an intraoral scanner; receiving one or more three-dimensional (3D) images of a face of the patient generated by a 3D image capture device during the intraoral scanning, wherein the intraoral scanner is captured in the one or more 3D images; and registering the one or more 3D images of the face of the patient to the first intraoral scan data based at least in part on a first position of the intraoral scanner relative to the face of the patient in the one or more 3D images.

A $12^{th}$ implementation may further extend the $11^{th}$ implementation. In the $12^{th}$ implementation, the one or more 3D images of the face of the patient are registered to the first intraoral scan data based further on a known second position of the intraoral scanner relative to the 3D surface in the first intraoral scan data generated by the intraoral scanner.

A 13$^{th}$ implementation may further extend the 12$^{th}$ implementation. In the 13$^{th}$ implementation, the one or more 3D images of the face of the patient are registered to the first intraoral scan data based further on a first orientation of the intraoral scanner relative to the face of the patient in the one or more 3D images and a known second orientation of the intraoral scanner relative to a 3D surface in the first intraoral scan data generated by the intraoral scanner.

A 14$^{th}$ implementation may further extend any of the 11$^{th}$ rough 13$^{th}$ implementations. In the 14$^{th}$ implementation the method further comprises generating a 3D model of at least one of face of the patient or the dental site using the one or more 3D images of the face of the patient and the first intraoral scan data of the dental site of the patient.

A 15$^{th}$ implementation may further extend any of the 11$^{th}$ rough 14$^{th}$ implementations. In the 15$^{th}$ implementation, the method further comprises: receiving a first 3D model of an upper dental arch of the patient and a second 3D model of a lower dental arch of the patient; generating a third 3D model of the face of the patient based on the one or more 3D images; and registering at least one of the first 3D model of the upper dental arch or the second 3D model of the lower dental arch to the third 3D model of the face based at least in part on the first position of the intraoral scanner relative to the face of the patient in the one or more 3D images.

A 16$^{th}$ implementation may further extend the 15$^{th}$ implementation. In the 16$^{th}$ implementation, the method further comprises: receiving second intraoral scan data of the upper dental arch and third intraoral scan data of the lower dental arch; generating the first 3D model of the upper dental arch based on the second intraoral scan data; and generating the second 3D model of the lower dental arch based on the third intraoral scan data.

A 17$^{th}$ implementation may further extend the 15$^{th}$ or 16$^{th}$ implementation. In the 17$^{th}$ implementation, the method further comprises: receiving second intraoral scan data of the dental site of the patient during the intraoral scanning by the intraoral scanner; receiving one or more additional 3D images of the face of the patient during the intraoral scanning, wherein the intraoral scanner is captured in the one or more additional 3D images, and wherein a position of the dental arch relative to the upper dental arch is different in the one or more additional 3D images than in the one or more 3D images; generating a fourth 3D model of the face of the patient based on the one or more additional 3D images; and registering at least one of the first 3D model of the upper dental arch or the second 3D model of the lower dental arch to the fourth 3D model of the face based at least in part on a second position of the intraoral scanner relative to the face of the patient in the one or more additional 3D images.

An 18$^{th}$ implementation may further extend the 15$^{th}$ rough 17$^{th}$ implementations. In the 18$^{th}$ implementation, the method further comprises: filtering out the intraoral scanner from at least one of the one or more 3D images of the face or the third 3D model of the face.

A 19$^{th}$ implementation may further extend the 15$^{th}$ rough 18$^{th}$ implementations. In the 19$^{th}$ implementation, the method further comprises: determining one or more soft tissue distortions caused by the intraoral scanner being inserted into a mouth of the patient; and modifying at least one of the one or more 3D images of the face or the third 3D model of the face to remove the one or more soft tissue distortions.

An 20$^{th}$ implementation may further extend the 15$^{th}$ rough 19$^{th}$ implementations. In the 20$^{th}$ implementation, the method further comprises: performing treatment planning to generate a fourth 3D model of the upper dental arch at a future stage of orthodontic or prosthodontic treatment and a fifth 3D model of the lower dental arch at the future stage of orthodontic or prosthodontic treatment; and generating a sixth 3D model of the face of the patient at the future stage of orthodontic or prosthodontic treatment showing how a smile of the patient will look at the future stage of orthodontic or prosthodontic treatment.

A 21$^{st}$ implementation may further extend any of the 11$^{th}$ rough 20$^{th}$ implementations. In the 21$^{st}$ implementation, a computer readable medium comprises instructions that, when executed by a processing device, cause the processing device to perform the operations of any of the 11$^{th}$ rough 20$^{th}$ implementations.

BRIEF DESCRIPTION OF THE DRAWINGS

Embodiments of the present disclosure are illustrated by way of example, and not by way of limitation, in the figures of the accompanying drawings.

FIG. 3A illustrates a flow diagram for a method of combining data from face scanning and intraoral scanning, in accordance with an embodiment.

FIG. 3B illustrates a flow diagram for a method of combining data from face scanning and intraoral scanning, in accordance with an embodiment.

FIG. 3C illustrates a flow diagram for a method of combining data from face scanning and intraoral scanning, in accordance with an embodiment.

FIG. 4A illustrates a flow diagram for a method of modifying a 3D model of a face, in accordance with an embodiment.

FIG. 4B illustrates a flow diagram for a method of generating a new model of a face at a future stage or orthodontic or prosthodontic treatment, in accordance with an embodiment.

FIG. 6 illustrates a flow diagram for a method of generating a facial characteristics model relating soft tissue to hard tissue, in accordance with an embodiment.

DETAILED DESCRIPTION

Figure 1:
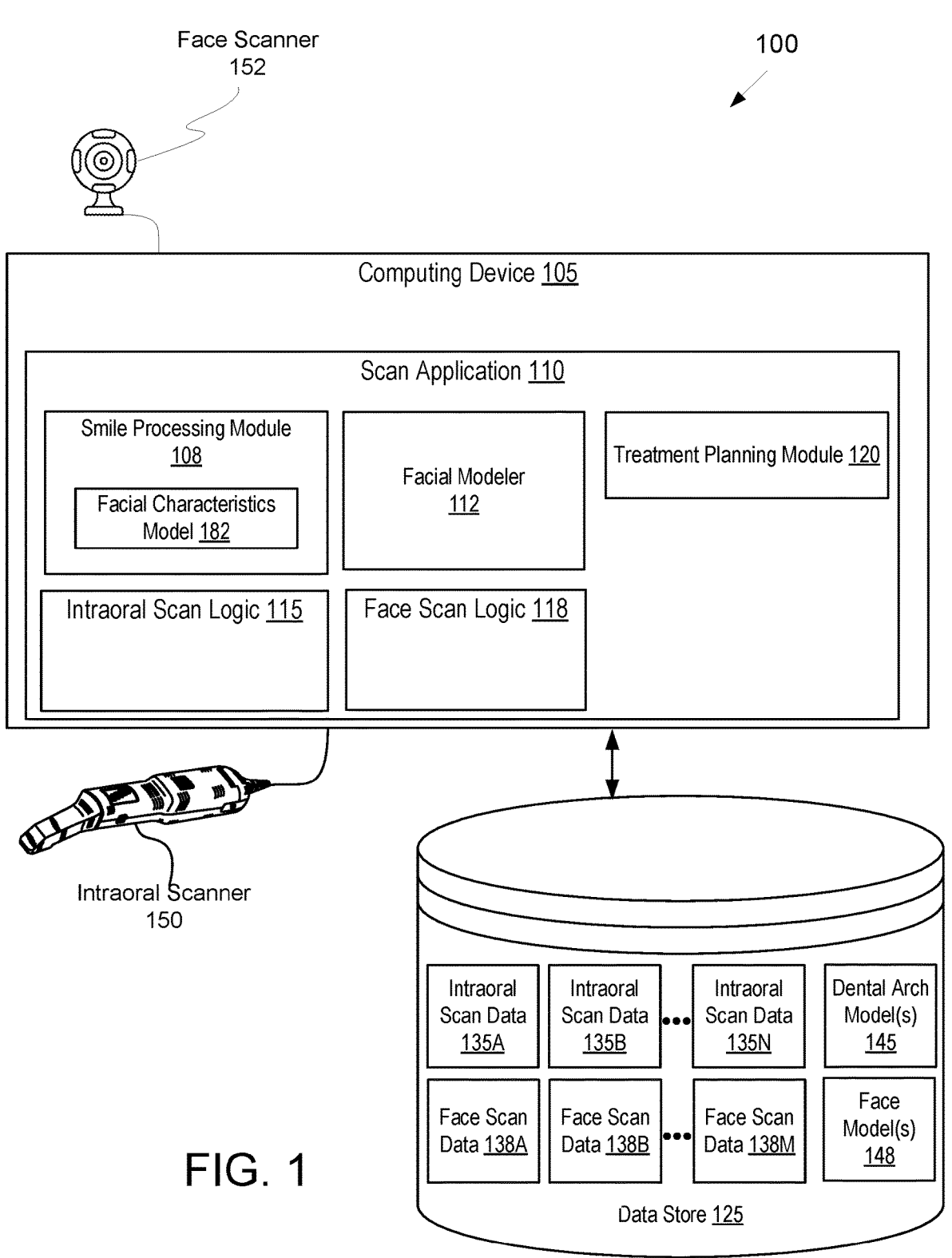
FIG. 1 illustrates one embodiment of a system for performing combined intraoral scanning and face scanning.

Described herein are methods and systems for combined intraoral scanning and face scanning. In embodiments, a three-dimensional (3D) image capture device may generate 3D images of a patient's face during intraoral scanning. During the intraoral scanning, an intraoral scanner may additionally generate intraoral scans of one or more dental sites of the patient (e.g., of a portion of the patient's upper and/or lower dental arches). The intraoral scanner may be captured in the 3D images of the patient's face. Data from the 3D images may be processed (e.g., using a trained machine learning model and/or image processing or point cloud processing algorithms) to identify the intraoral scanner in the 3D images. The position and/or orientation of the intraoral scanner in the 3D images relative to the patient's face (e.g., relative to a nose and eyes of the patient) may be used to determine how to register the 3D images to the intraoral scans. In some embodiments, 3D models of the upper and/or lower dental arches of the patient may have been generated based on prior intraoral scans or may be generated based on the currently generated intraoral scans. Additionally, a 3D model of the patient's face may be generated based on the 3D images of the patient's face. The 3D models of the upper and/or lower dental arches may be registered to the 3D model of the face based on the determined position and/or orientation of the intraoral scanner in the 3D images of the patient's face (and/or in the 3D model of the patient's face).

Embodiments enable the registration of intraoral scans to 3D images of a patient's face (face scans) and enable the registration of 3D models of upper and lower dental arches to 3D models of a patient's face. As the patient moves their lower jaw and makes different facial expressions, new 3D models of the patient's face may be generated, and those new 3D models may be registered to the models of the upper and lower dental arches, which may have different relative positions and orientations after registration to each of the new 3D models of the face. Embodiments add additional capabilities to a scan application that can replace special hardware traditionally used for jaw motion analysis. Embodiments further enable a patient jaw to be integrated into 3D face scans, which can be used to simulate orthodontic and/or prosthodontic treatments. In embodiments, a mandibular motion envelope may be determined (e.g., by having a patient move their lower jaw through extremes). The mandibular motion envelope may then be used together with the combined 3D face model and 3D upper/lower dental arch models to analyze and simulate various clinical situations.

Various embodiments are described herein. It should be understood that these various embodiments may be implemented as stand-alone solutions and/or may be combined. Accordingly, references to an embodiment, or one embodiment, may refer to the same embodiment and/or to different embodiments. Additionally, some embodiments are discussed with reference to restorative dentistry, and in particular to preparation teeth and margin lines. However, it should be understood that embodiments discussed with reference to restorative dentistry (e.g., prosthodontics) may also apply to corrective dentistry (e.g., orthodontics). Similarly, embodiments discussed with reference to corrective dentistry (e.g., orthodontics) may also apply to restorative dentistry.

FIG. 1 illustrates one embodiment of a system 100 for performing intraoral scanning and facial scanning. In one embodiment, one or more components of system 100 carries out one or more operations described below with reference to FIGS. 3A-5C.

System 100 may be located at a dental office. System 100 may include an intraoral scanner 150 and a face scanner 152 connected to a computing device 105. The intraoral scanner 150 and/or face scanner 152 may be connected to the computing device via wired and/or wireless connections. In one embodiment, the face scanner 152 and/or intraoral scanner 150 are connected to the computing device 105 via a network. The network may be a local area network (LAN), a public wide area network (WAN) (e.g., the Internet), a private WAN (e.g., an intranet), or a combination thereof. The network may be a wired network, a wireless network, or a combination thereof.

Computing device 105 may further be coupled to (e.g., via a wired or wireless connection) or include a data store 125. The data store 125 may be a local data store or a remote data store. Computing device 105 may include one or more processing devices, memory, secondary storage, one or more input devices (e.g., such as a keyboard, mouse, tablet, and so on), one or more output devices (e.g., a display, a printer, etc.), and/or other hardware components.

Intraoral scanner 150 may include a probe (e.g., a hand held probe) for optically capturing three-dimensional structures of dental sites. The intraoral scanner 150 may be used to perform intraoral scanning of a patient's oral cavity.

Face scanner 150 may include a 3D image capture device for optically capturing 3D images of a patient's face, and may include a color camera (e.g., a high-resolution two-dimensional color camera). Face scanner 150 may generate images and/or video (e.g., one or more stream of images, such as a first stream of color 2D images and a second stream of 3D images). The 3D image capture device may use structured light projection, stereo imaging and/or other techniques for 3D image capture. For example, the face scanner 150 may include a camera (e.g., having one or more complementary metal oxide semiconductor (CMOS) or charge coupled device (CCD) sensors) and a structured light projector. The structured light projector may project structured light onto the patient's face, and the structured light on the patient's face may be captured by the camera. Distortions of the structured light may be used to determine a 3D surface of the patient's face. In another example, the face scanner 150 may include two or more cameras separated by a known distance. The cameras may be monochrome or color cameras. The two or more cameras may each take 2D images of the patient's face, and the 2D images of the two or more cameras may be combined to generate 3D images using conventional stereo imaging techniques. In some embodiments, face scanner 150 generates 2D images or video rather than, or in addition to, 3D images or video.

Computing device 105 may include a scan application 110 that includes intraoral scan logic 115 and face scan logic 120. The scan application 110 may additionally include one or more of a smile processing module 108, a facial modeler 112, and/or a treatment planning module 120. Any of the modules and/or logics of the scan application 110 may be standalone applications and/or logics (e.g., that are not part of the scan application 110) in some embodiments. Additionally, any of the modules and/or logics of the scan application 110 may be combined into a single module or logic in some embodiments.

Intraoral scan logic 115 running on computing device 105 may communicate with the intraoral scanner 150 to effectuate an intraoral scan of a patient's oral cavity. A result of the intraoral scan may be intraoral scan data 135A, 135B through 135N that may include one or more sets of intraoral scans. Each intraoral scan (also referred to as an intraoral image) may be or include a two-dimensional (2D) or 3D point cloud or image that includes depth information of a portion of a dental site, and may include x, y and z information. In one embodiment, the intraoral scanner 150 generates numerous discrete (i.e., individual) intraoral scans. Sets of discrete intraoral scans may be merged into a smaller set of blended intraoral scans, where each blended scan is a combination of multiple discrete scans or images. The intraoral scanner 150 may transmit the intraoral scan data 135A, 135B through 135N to the computing device 105. Computing device 105 may store the intraoral scan data 135A-135N in data store 125.

Face scan logic 118 running on computing device 105 may communicate with the face scanner 152 to effectuate a scan of the patient's face. Such a scan of the patient's face may be performed during at least a portion of the intraoral scanning. A result of the face scan may be face scan data 138A, 138B through 138M that may include one or more face scans and/or color 2D images of a patient's face. Each face scan (also referred to as a 3D image of a patient's face) may be or include a two-dimensional (2D) or 3D point cloud or image that includes depth information of a patient's face, and may include x, y and z information in a different reference frame than the x, y and z information of the intraoral scans. The face scanner 152 may transmit the face scan data 138A, 138B through 138M to the computing device 105. Computing device 105 may store the face scan data 138A-138M in data store 125.

According to an example, a user (e.g., a practitioner) may subject a patient to intraoral scanning in a field of view of face scanner 152. In doing so, the user may apply intraoral scanner 150 to one or more patient intraoral locations. The intraoral scanning may be divided into one or more segments. As an example, the segments may include a lower buccal region of the patient, a lower lingual region of the patient, an upper buccal region of the patient, an upper lingual region of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such intraoral scanner application, the intraoral scanner 150 may provide intraoral scan data 135A-N to computing device 105. The intraoral scan data 135A-N may be provided in the form of intraoral scan or image data sets, each of which may include 2D intraoral images and/or 3D intraoral scans of particular teeth and/or regions of an intraoral site. In one embodiment, separate data sets are created for the maxillary arch, for the mandibular arch, for a patient bite, and for each preparation tooth. Alternatively, a single large intraoral data set is generated (e.g., for a mandibular and/or maxillary arch). Such scans may be provided from the scanner to the computing device 105 in the form of one or more points (e.g., one or more pixels and/or groups of pixels). For instance, the scanner 150 may provide such a 3D scan as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Additionally, the manner in which the oral cavity is to be scanned may depend on a doctor's scanning preferences and/or patient conditions. For example, some doctors may perform intraoral scanning (e.g., in a standard scanning mode) after using a retraction cord to expose a margin line of a preparation. Other doctors may use a partial retraction scanning technique in which only portions of the margin line are exposed and scanned at a time (e.g., performing scanning in a partial retraction scanning mode).

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

Throughout at least a portion of the intraoral scanning process, face scanner 152 generates face scans (e.g., 3D images of the patient's face) and/or color images of a patient's face. Face scans and/or color images (e.g., color 2D images) of a patient's face may also be generated before and/or after the intraoral scanning (e.g., with no intraoral scanner in the field of view of the face scanner 152). Since at least some of the face scans are generated during the intraoral scanning and while the intraoral scanner 150 is in the field of view of the face scanner 152, at least some of the face scans include a depiction of the intraoral scanner (e.g., the intraoral scanner may be captured together with the patient's face in the face scans).

During intraoral scanning, intraoral scan logic 115 may generate a 3D surface of a dental site by stitching together multiple intraoral scans or images. Once a scan session is complete (e.g., all scans for an intraoral site or dental site have been captured), intraoral scan logic 115 may generate a virtual 3D model of one or more scanned dental sites (e.g., of the upper and lower dental arches or jaws of the patient). To generate the virtual 3D model of the dental site(s), intraoral scan logic 115 may register and "stitch" or merge together the intraoral scans or images generated from the intraoral scan session. In one embodiment, performing registration includes capturing 3D data of various points of a surface in multiple scans or images (views from a camera), and registering the scans or images by computing transformations between the scans or images. In one embodiment, the 3D data may be in the form of multiple height maps, which may be projected into a 3D space of a 3D model to form a portion of the 3D model. In one embodiment, the 3D data may be in the form of 3D point clouds. The scans or images may be integrated into a common reference frame by applying appropriate transformations to points of each registered scan or image and projecting each scan or image into the 3D space.

In one embodiment, registration is performed for adjacent or overlapping intraoral scans or images (e.g., each successive frame of an intraoral video). In one embodiment, registration is performed using blended scans or images. Registration algorithms are carried out to register two adjacent intraoral scans or images (e.g., two adjacent blended intraoral scan or images) and/or to register an intraoral scan or image with a 3D model, which essentially involves determination of the transformations which align one scan or image with the other scan or image and/or with the 3D model. Registration may involve identifying multiple points in each scan or image (e.g., point clouds) of a scan or image pair (or of a scan or image and the 3D model), surface fitting to the points, and using local searches around points to match points of the two scans or images (or of the scan or image and the 3D model). For example, intraoral scan logic 115 may match points of one scan or image with the closest points interpolated on the surface of another scan or image, and iteratively minimize the distance between matched points. Other registration techniques may also be used.

Intraoral scan logic 115 may repeat registration for all intraoral scans or images of a sequence of intraoral scans or images to obtain transformations for each intraoral scan or image, to register each scan or image with the previous one and/or with a common reference frame (e.g., with the 3D model). Intraoral scan logic 115 integrates all intraoral scans or images into one or more virtual 3D model or surface 145 by applying the appropriate determined transformations to each of the scans or images. Each transformation may include rotations about one to three axes and translations within one to three planes.

The registration and stitching performed during scanning to produce the 3D surface of the dental site (e.g., of the upper or lower dental arch) may be a similar registration and stitching process to the process that is performed after scanning to produce the 3D model. However, the registration and stitching performed to produce the 3D model may be more time consuming and take more processing power than that performed to produce the 3D surface. Accordingly, the 3D surface may be periodically or continuously updated during scanning of the dental site. In one embodiment, the 3D surface of the dental site is updated in real time or near-real time as scanning is performed to provide a user with visual feedback as to scanning progress. Any embodiments discussed herein with reference to 3D models also apply equally to 3D surfaces.

Face scan logic 118 receives face scan data 138A-M, some of which are generated during the intraoral scanning (i.e., during capture of at least some of intraoral scan data 135A-N). Unlike intraoral scan data 135A-N, which includes many scans each of which captures just a small portion of a dental site, each face scan data 138A-M may include data for a patient's full face. Accordingly, a 3D model or 3D surface of the patient's face (face model(s) 148) may be generated from a single face scan and/or color image of a patient's face (e.g., from just face scan data 138A) or from a few face scans and/or color images of a patient's face. In some embodiments, each face scan (e.g., each of face scan data 128A, face scan data 13813, etc.) represents or is used to generate a separate 3D model of the patient's face (e.g., a different face model 148). The 3D models of the patient's face 148 may differ based on the patient moving their jaw, changing their facial expression, and so on.

In embodiments, one or more (e.g., each) face model 148 may be registered to one or more dental arch models 145 by face scan logic 118. Additionally, intraoral scan data 135A-N may be registered to respective face scan data 138A-M generated at the same time as the intraoral scan data 135A-N by face scan logic 118. For example, if intraoral scan data 135A and face scan data 138A were generated at the same time (or while the scanner was at a same position relative to the patient's face), then intraoral scan data 135A may be registered to face scan data 138A. Face models 148 may be registered to dental arch models 145 (and face scan data 138A-M may be registered to intraoral scan data 135A-N) in a similar manner to how intraoral scans are registered to one another in some embodiments.

Face scan logic 118 may generate a 3D surface of a patient's face from a single face scan or from multiple face scans generated close together in time. Each of these face scans may include a representation of the intraoral scanner. Face scan logic 118 may determine a position and orientation of the intraoral scanner in the face scan(s) and/or face model 148. The position and orientation of the intraoral scanner may be determined relative to one or more facial features, such as the patient's nose, the patient's eyes, etc., which may be approximately static relative to the upper dental arch of the patient. A position and/or orientation of the intraoral scanner may be known relative to 3D surfaces in intraoral scan data 135A-N generated by the intraoral scanner 150 (e.g., based on prior calibration of the intraoral scanner 150). Accordingly, the known position and/or orientation of the 3D surface in the intraoral scans relative to the intraoral scanner and the determined relative position and/or orientation of the intraoral scanner relative to the facial features of the patient's face may be used to register the intraoral scan (e.g., the 3D surface of the dental site represented in the intraoral scan) to the face scan. Similarly, the intraoral scan may be registered to the 3D model of the patient's face 148 generated based on face scan data captured while the intraoral scan was captured. As a result, the intraoral scan data (e.g., a 3D surface of a dental site captured in the intraoral scan data) may be added to the 3D model of the patient's face in embodiments.

In some embodiments, intraoral scanning may have been started prior to the start of data capture by the face scanner 152. The intraoral scan data resulting from such intraoral scanning may be used to generate a 3D model of the patient's upper dental arch and a separate 3D model of the patient's lower dental arch. The intraoral scan data 135A-N may then be generated after the 3D models of the upper and/or lower dental arch are generated. The intraoral scan data may then be used to register the 3D model of the upper dental arch and the 3D model of the lower dental arch to the 3D model of the face (face model 148). Each face model may have a different relative position/orientation of the upper and lower dental arches/jaws, and so the 3D model of the upper dental arch and the 3D model of the lower dental arch may have different relative positions and orientations for each 3D model of the patient's face.

In some embodiments, intraoral scanning and face scanning are performed in parallel. There may be insufficient information to generate a full 3D model of an upper or lower dental arch during much of the scanning. However, after enough intraoral scans have been captured that are sufficient to generate a full 3D model of the upper and/or lower dental arch, that full 3D model may be generated and then registered to the 3D face models generated at an earlier time before the 3D model of the dental arch(es) was ready based on the intraoral scans generated commensurate with the face scan used to generate the 3D face model. For example, at the start of intraoral scanning only a few intraoral scans of an upper dental arch may have been captured. The face scan generated at the time that these intraoral scans were generated may be registered to the intraoral scans, and a 3D model of the face may be generated for that face scan (or the face scan may itself be a 3D model of the patient's face) but there may be no 3D model of the upper or lower dental arch to register to the 3D model of the face generated from the face scan. After further intraoral scanning, enough intraoral scans may have been captured to generate a full 3D model of the upper dental arch. The full 3D model of the upper dental arch may then be registered to the earlier generated 3D model of the patient's face generated at the start of intraoral scanning.

In one embodiment, performing registration between the intraoral scans and the face scans (or between the dental arch models and the face models) includes capturing 3D data of various points of a surface in the face scan/model, and using that information together with known information about the relative position/orientation of the intraoral scanner to 3D surfaces in intraoral scans captured by the intraoral scanner to register the intraoral scans to the face scan/model by computing transformations therebetween. In one embodiment, the 3D data of the face scans may be in a first reference frame. However, the 3D data of the intraoral scans may each be in a second reference frame, and the reference frame of each intraoral scan may be different from the reference frames of other intraoral scans due to the changing position/orientation of the intraoral scanner during intraoral scanning. In one embodiment, the 3D data of the face scans may be in the form of 3D point clouds. The face scans or 3D images (and/or face models) and the intraoral scans (and/or 3D surfaces and/or 3D models generated from intraoral scans) may be integrated into a common reference frame by applying appropriate transformations to points of each registered scan or image and projecting each scan or image into a common 3D space.

In some embodiments, intraoral scanner 150 includes one or more fiducials or easily captured features that facilitate accurate identification of the position and orientation of the intraoral scanner 150 in face scan data 138A-M. Face scan data 138A-M may be processed by face scan logic 118 using one or more image processing or point cloud processing algorithms designed to identify the fiducials/features of the intraoral scanner 150 in the face scan data 138A-M. The image processing or point cloud processing algorithms may output a position and orientation of the intraoral scanner 150 in the face scans to a high degree of accuracy (e.g., accurate to within 0.5 mm, accurate to within 50 microns, etc.). In some embodiments, face scan logic 118 includes a trained machine learning model that has been trained to perform object recognition of intraoral scanner 150 in face scan data 138A-M and to determine a precise location and orientation of the intraoral scanner 150 in the face scan data 138A-M. In such embodiments, the intraoral scanner 150 may or may not include features or fiducials added to a body of the intraoral scanner (or to a protective sleeve placed around a probe of the intraoral scanner 150) for identification of the intraoral scanner.

One type of machine learning model that may be used for the tool recognition is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize that the image contains a face or define a bounding box around teeth in the image.

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and back-propagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

Training of the machine learning model and use of the trained machine learning model (e.g., for the excess material removal algorithm and/or the excess gingiva removal algorithm) may be performed by processing logic executed by a processor of a computing device. For training of the machine learning model, a training dataset containing hundreds, thousands, tens of thousands, hundreds of thousands or more images should be used to form a training dataset. A training dataset may be gathered, where each data item in the training dataset may include an image or scan and an associated label that identifies pixels or points associated with one or more classes of tools. Alternatively, the model may output a map indicating which points or pixels are classified as a tool. A shape of the tool may be determined from those pixels or points and then used to perform a lookup in a tool library to identify the detected tool.

A machine learning model may be trained using the scans or images or 3D models with the labeled intraoral scanner information. The machine learning model may be trained to classify pixels or points in images or point clouds as belonging to one or more classes (e.g., intraoral scanner, not intraoral scanner, etc.). The result of this training is a function that can identify a position/orientation of the intraoral scanner in face scans and/or face models. In particular, the machine learning model may be trained to generate a probability map, where each point in the probability map corresponds to a pixel or point of an input image or scan or model and indicates one or more of a first probability that the pixel or point represents an intraoral scanner, a second probability that the pixel or point represents a patient face, and so on. In embodiments, the machine learning model may also be trained to identify facial features, such as nose, eyes, etc.

During an inference stage (i.e., use of the trained machine learning model), the face scan or scans (and optionally other data) is input into the trained model, which may have been trained as set forth above. The trained machine learning model outputs a probability map, where each point in the probability map corresponds to a pixel or point in the face scan or image or model and indicates probabilities that the pixel represents an intraoral scanner or a patient's face.

In one embodiment, the probability map is used to update the face scan (or 3D surface/model generated therefrom) to generate a modified face scan or face model. The probability map may be used to determine pixels or points that represent an intraoral scanner. Data for pixels or points labeled as an intraoral scanner may then be removed from or hidden in the face image/scan and/or the face model.

The treatment planning module 120 is responsible for generating a treatment plan that includes a treatment outcome for a patient. The treatment plan may include a prosthodontic treatment and/or an orthodontic treatment. The treatment plan may include and/or be based on intraoral scan data 135A-N, face scan data 138A-M, dental arch model(s) 145 and/or face model(s) 148. The treatment planning module 120 may determine current positions and orientations of the patient's teeth from the virtual 3D model (s) and determine target final positions and orientations for the patient's teeth represented as a treatment outcome. The treatment planning module 120 may then generate one or more virtual 3D model (e.g., dental arch model) showing the patient's dental arches at the end of treatment and optionally one or more virtual 3D models showing the patient's dental arches at various intermediate stages of treatment. These various virtual 3D models may be included in the treatment plan. Additionally, face models 148 may be determined for one or more stages of treatment.

By way of non-limiting example, a treatment outcome may be the result of a variety of dental procedures. Such dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as implants, crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. Any of treatment outcomes or updates to treatment outcomes described herein may be based on these orthodontic and/or dental procedures. Examples of orthodontic treatments are treatments that reposition the teeth, treatments such as mandibular advancement that manipulate the lower jaw, treatments such as palatal expansion that widen the upper and/or lower palate, and so on. For example, an update to a treatment outcome may be generated by interaction with a user to perform one or more procedures to one or more portions of a patient's dental arch or mouth. Planning these orthodontic procedures and/or dental procedures may be facilitated by the AR system described herein.

A treatment plan for producing a particular treatment outcome may be generated by first performing an intraoral scan of a patient's oral cavity to generate image data comprising multiple 3D images of the patient's upper and lower dental arches. Alternatively, a physical mold may be taken of the patient's upper and lower dental arches, and a scan may be performed of the mold. From the intraoral scan (or scan of the mold) a virtual 3D model (e.g., dental arch model(s) 145) of the upper and/or lower dental arches of the patient may be generated. A dental practitioner may then determine a desired final position and orientation for the patient's teeth on the upper and lower dental arches, for the patient's bite, and so on. This information may be used to generate the virtual 3D model(s) of the patient's upper and/or lower arches after orthodontic treatment. This data may be used to create, for example, and orthodontic treatment plan. The orthodontic treatment plan may include a sequence of orthodontic treatment stages. Each orthodontic treatment stage may adjust the patient's dentition by a prescribed amount, and may be associated with a 3D model of the patient's dental arch that shows the patient's dentition at that treatment stage.

In some embodiments, the treatment planning module 120 may receive or generate one or more virtual 3D models, virtual 2D models, or other treatment outcome models based on received intraoral scans and/or face scans. For example, an intraoral scan of the patient's oral cavity may be performed to generate an initial virtual 3D model of the upper and/or lower dental arches of the patient. Treatment planning module 120 may then determine a final treatment outcome based on the initial virtual 3D model, and then generate a new virtual 3D model representing the final treatment outcome.

Scan application 110 may generate 3D face models 148 of the patient's face as well as 3D upper and lower dental arch models 145, and may display the 3D models/surfaces to a user (e.g., a doctor) via a user interface. Such 3D face models 145 may be associated with different stages of treatment in some embodiments. The 3D models/surfaces can then be checked visually by the doctor. The doctor can virtually manipulate the 3D models/surfaces via the user interface with respect to up to six degrees of freedom (i.e., translated and/or rotated with respect to one or more of three mutually orthogonal axes) using suitable user controls (hardware and/or virtual) to enable viewing of the 3D model/ surface from any desired direction. In one embodiment, the doctor may control an opacity and/or other visualization of the 3D model of the face vs. the 3D models of the dental arches. For example, via the user interface the doctor may choose the make the 3D model of the face mostly transparent (e.g., 80% or 90% transparent) so that the dental arches and their respective orientations and/or positions may be easily viewed while still seeing how soft facial tissue of the 3D face model relates to the dental arches.

Insertion of the intraoral scanner 150 in part of the patient's mouth can cause a distortion of the patient's soft facial tissue. For example, the lips and cheeks on a right side of the patient's mouth may stretch around the intraoral scanner when the probe of the intraoral scanner is placed in the right side of the mouth. The lips and cheeks on the left side of the patient's mouth may be unaffected by such insertion of the intraoral scanner probe in the right hand side of the mouth. Similarly, while the intraoral scanner probe is placed in the left side of the mouth, the lips and cheeks on the left side of the mouth may be distended while the lips and cheeks on the right side of the mouth are largely unaffected.

In embodiments, facial modeler 112 uses the one or more of intraoral scan data 135A-N, dental arch models 145, face scan data 138A-M and/or face models 148 to generate a facial characteristics model for a patient. Facial modeler 112 may additionally use a treatment plan generated by treatment planning module 120 to generate a facial characteristics model 182 for the patient in some embodiments. To generate the facial characteristics model, the facial modeler 112 may generate one or more mapping between the positions of visible landmarks associated with teeth of the patient and visible landmarks associated with facial features (e.g., eyes, nose, lips, etc. of the patient). The visible landmarks may be landmarks that will show up in an optical image (e.g., such as points on one or more teeth of the patient). The first mapping may also be between current and final positions of one or more non-visible landmarks of bony structures that might not show up in, for example, the face scan data 138A-M. Bony structures and/or soft tissues may be used as visible and/or non-visible landmarks. Examples of bony structures include teeth, upper and lower jaw bones, cheek bones, skull, and so on. Examples of soft tissues include lips, gums, skin (e.g., subcutaneous layer, cutaneous layer, etc.), muscles, fat, ligaments, and so on. The soft tissues may show, for example, lip protrusion, facial contours, smile line, and so on.

At least one mapping may be between first visible landmarks associated with teeth and/or bony structures and second visible landmarks associated with soft tissues on the patient's face. For example, the mapping may be between points on teeth and points on the cheeks and/or on the lips, and so on. The mapping may additionally map non-visible landmarks of bony structures to non-visible landmarks of soft tissues (e.g., internal soft tissues such as muscles, internal skin layers, ligaments, and so on). The mapping may be used to determine final positions of the landmarks post-treatment when combined with a treatment plan in embodiments.

Facial modeler 112 may generate a facial characteristics model 182 that includes the one or more mappings. The facial characteristics model 182 may additionally generate functions that affect the relationships between first landmarks (e.g., teeth) and second landmarks (e.g., nose, lips, etc.) for different facial expressions. Different functions may be generated for different sets of landmarks. The functions that affect the relationships between the first landmarks and the second landmarks may be generated based on face scan data 138A-M, based on historical data for other patients and/or based on pedagogical data (e.g., data describing how different facial tissues respond to jaw motion). In one embodiment, the functions are generic functions generated based on historical and/or pedagogical data.

In some embodiments, the facial characteristics model 182 includes additional information based on a cephalometric analysis of the patient. Facial modeler 112 may determine one or more cephalometric characteristics based on received face scan data 138A-M. The cephalometric characteristics may include one or more distances or angles describing the position of features of the patient's face relative to each other. In some embodiments, the facial modeler 112 may estimate changes to the cephalometric characteristics based on a treatment outcome for the patient.

Once the facial characteristics model 182 is generated, it may be provided to a smile processing module 108. The smile processing module 108 may then process face models 148 and/or dental arch models 145 using the facial characteristics model 182 to generate updated face models 148 in which facial distortions caused by insertion of the intraoral scanner 150 into the patient's oral cavity have been removed. In some embodiments, post-treatment dental arch models may be input into the facial modeler 112 (optionally together with one or more face models 148) to generate new face models representing a patient's face and smile post-treatment.

Face scanner 152 may generate an image or video of user smiling while intraoral scanner 150 is inserted into the patient's mouth. The generated image (or sequence of images) may show a current pre-treatment dentition and facial features of the patient, which may include one or more malocclusions, lip protrusion, a narrow smile showing dark triangles at the corners of the mouth where the smile extends beyond the teeth, and so on. Smile processing module 108 may process the captured image (or images) using the facial characteristics model 182 to generate one or more post-treatment facial images and/or models of the patient. These one or more post-treatment facial images and/or models may then be output to a display to show the patient and/or the dentist the patient's post-treatment smile.

In one embodiment, smile processing module 108 outputs instructions for the patient to adopt a series of different facial expressions. Face scanner 152 may capture images of each of these facial expressions. Facial modeler 112 may use these captured images of the facial expressions to update or refine one or more functions that model the interaction between bony structures and facial tissues with changing expressions. Alternatively, facial modeler 112 may use the one or more images to generate the functions if they have not already been generated (e.g., if facial characteristics model 182 has not yet been generated). In one embodiment, facial modeler 112 replaces weights and/or parameters of one or more functions to replace generic functions with user specific functions. Such user specific functions may model the actual mechanics of how different soft tissues of the patient respond to facial expressions and movements. Once the one or more functions are updated (or generated), facial modeler 112 may generate an updated or new facial characteristics model 182 that may include the first mapping, the second mapping and the one or more functions. Smile processing module 108 may then use the updated or new facial characteristics model 182 to generate accurate photo-realistic post-treatment images and/or models of the patient.

In some embodiments, a patient may be asked to move their face/jaw through various facial expressions and/or extremes during intraoral scanning and face scanning. Such facial positions and/or extremes of the jaw may be used to compute a mandibular motion envelope. In embodiments, the mandibular motion envelope may be used together with generated 3D models of faces, 3D models of dental arches, and/or registration of 3D models of faces to 3D models of dental arches for various purposes, such as for treatment planning, simulation and analysis of various clinical situations, and so on. In some embodiments, occlusal contacts between teeth of the upper dental arch and teeth of the lower dental arch may be estimated for each 3D model of the face (and positions/orientations of the 3D models of the upper and lower dental arches registered to the 3D model of the face). The registered 3D model of the face and 3D models of the upper and lower dental arches may be used to determine, for example, a patient's midline and how it relates to the patient's teeth.

In some embodiments, a doctor may input an instruction or make a selection to enter a combined scanning mode in which intraoral scanning is performed at the same time as face scanning. The doctor may also select to perform standard scanning in which no face scanning is performed.

Figure 2:
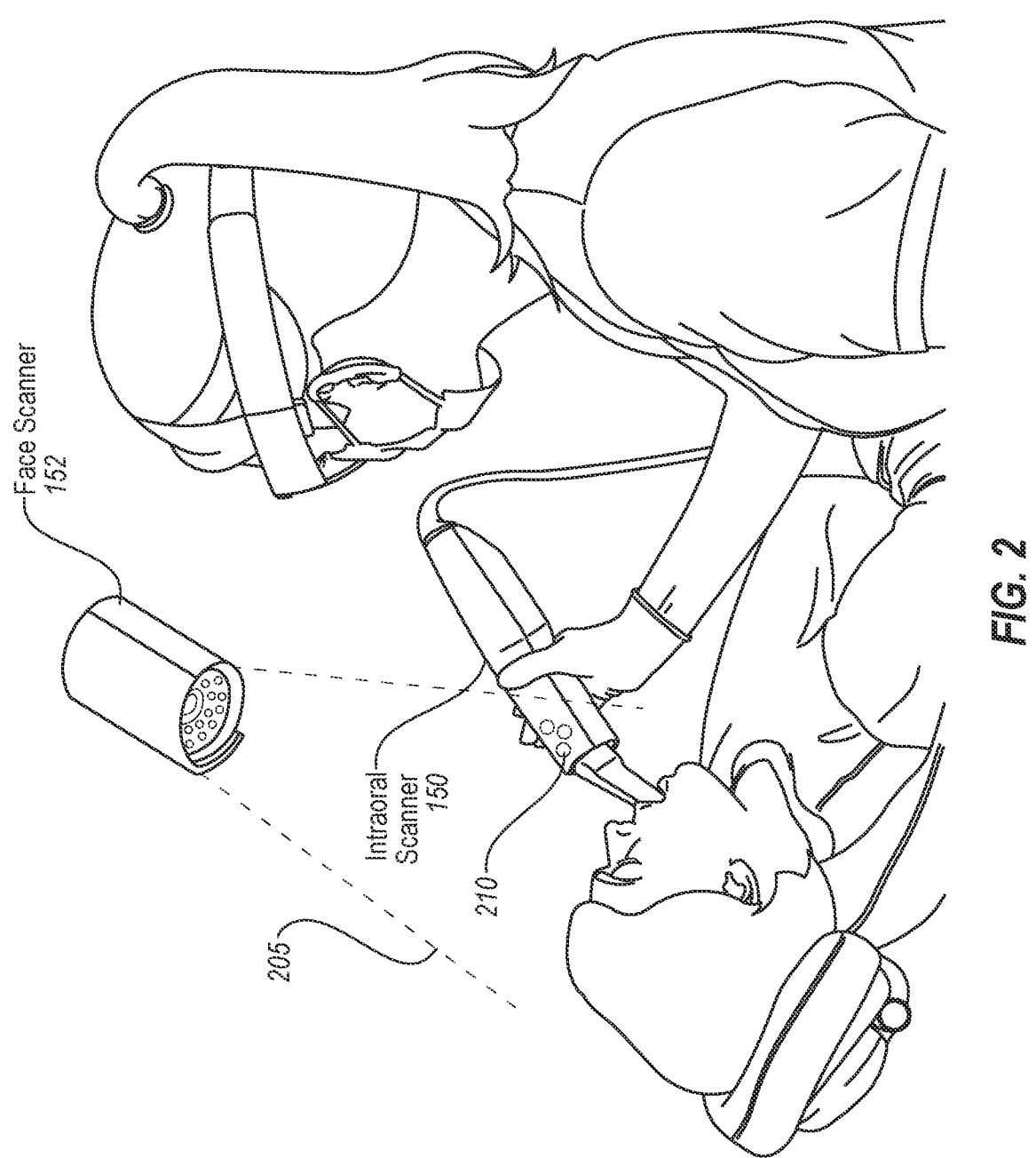
FIG. 2 illustrates the system of FIG. 1 in operation, in accordance with an embodiment.

FIG. 2 illustrates the system of FIG. 1 in operation, in accordance with an embodiment. As shown, a doctor has inserted an intraoral scanner 150 into the patient's mouth and begun intraoral scanning. The intraoral scanner 152 and patient's face are in the field of view 205 of the face scanner 152. During the intraoral scanning, face scanner 152 generates 3D images of the face of the patient and of the intraoral scanner 150. As shown, the intraoral scanner 150 may include one or more fiducials or features 210 that enable the intraoral scanner 150 to be easily identified and a position and orientation of the intraoral scanner 150 to be determined in 3D images (or 2D images) generated by face scanner 152.

FIGS. 3A-4B illustrate methods related to combined intraoral scanning and face scanning. The methods may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the methods are performed by a computing device executing scan application 110.

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

FIG. 3A illustrates a flow diagram for a method 300 of combining data from face scanning and intraoral scanning, in accordance with an embodiment. At block 302 of method 300, processing logic receives intraoral scan data of a dental site of a patient during intraoral scanning by an intraoral scanner. The intraoral scan data may be generated by the intraoral scanner during intraoral scanning and sent to a processing device executing the processing logic. The dental site may be, for example, a portion of an upper and/or lower dental arch of the patient.

At block 304, processing logic receives one or more 3D images (e.g., face scan data 138A-M) of a face of the patient generated by a 3D image capture device (e.g., face scanner 152) during the intraoral scanning. The intraoral scanner may be captured in the one or more 3D images of the face. At block 305, processing logic determines a position and/or orientation of the intraoral scanner in the 3D image(s) of the face. Such a determination of the position/orientation of the intraoral scanner may be determined based on application of one or more image processing or point cloud processing algorithms and/or trained machine learning models to the 3D image(s) of the face.

At block 306, processing logic registers the one or more 3D images of the face of the patient to the intraoral scan data based at least in part on a first position and/or orientation of the intraoral scanner relative to the face of the patient in the one or more 3D images. The one or more 3D images (3D face scan) of the patient may have been generated at or around the same time that the intraoral scan data was generated. A transformation between the intraoral scanner position/orientation and the position/orientation of 3D surfaces in the intraoral scan data may be known. Accordingly, the relative position and/or orientation of the intraoral scanner relative to the patient's face in the 3D image(s) may be used together with the known transformation between the intraoral scanner position/orientation and the position/orientation of the 3D surfaces in the intraoral scan data to determine a transformation between the intraoral scan data and the 3D image(s). Such determined transformations may be used to register the intraoral scan data to the 3D image(s).

Method 300 may be repeated one or more times during intraoral scanning. For example, as each 3D image of a face is generated, method 300 may be performed to register that 3D image of the patient's face to associated intraoral scan data of the patient's oral cavity.

FIG. 3B illustrates a flow diagram for a method 310 of combining data from face scanning and intraoral scanning, in accordance with an embodiment. At block 312 of method 310, processing logic receives a 3D model of a patient's upper dental arch and a 3D model of the patient's lower dental arch. Alternatively, processing logic may receive intraoral scans and then use the intraoral scans to generate the 3D models of the upper and lower dental arches.

At block 314, processing logic receives intraoral scan data of a dental site of the patient during intraoral scanning by an intraoral scanner. The intraoral scan data may be generated by the intraoral scanner during intraoral scanning and sent to a processing device executing the processing logic. The dental site may be, for example, a portion of the upper and/or lower dental arch of the patient.

At block 316, processing logic receives one or more 3D images (e.g., face scan data 138A-M) of a face of the patient generated by a 3D image capture device (e.g., face scanner 152) during the intraoral scanning. The intraoral scanner may be captured in the one or more 3D images of the face.

At block 318, processing logic may generate a 3D model of the patient's face based on the one or more 3D images of the face. Alternatively, the 3D image(s) may themselves constitute a 3D model of the patient's face. At block 319, processing logic determines a position and/or orientation of the intraoral scanner in the 3D image(s) and/or the 3D model of the face. Such a determination of the position/orientation of the intraoral scanner may be determined based on application of one or more image processing algorithms, point cloud processing algorithms, and/or trained machine learning models to the 3D image(s) and/or the 3D model of the face.

At block 320, processing logic registers the 3D models of the upper and lower dental arch of the patient to the 3D model of the face based on at least one of a) information from the one or more 3D images (e.g., a determined position and orientation of the intraoral scanner in the 3D image(s), b) information form the intraoral scan data (e.g., 3D surfaces in the intraoral scan data that registered to 3D surfaces in the 3D models of the upper and/or lower dental arch), or c) known position and/or orientation of the intraoral scanner to a scanned 3D surface in the intraoral scan data. For example, a position/orientation of the intraoral scanner in the 3D image(s) of the face and/or in the 3D model of the face may be determined. The position/orientation of the intraoral scanner in the 3D image(s) and/or 3D model of the face may be used together with the known relative position/orientation of the intraoral scanner to intraoral scans generated by the intraoral scanner to register the 3D model of the face to the intraoral scan data. The intraoral scan data may further be registered to the 3D models of the upper and/or lower dental arch based on the same features/surfaces being recognized between the intraoral scan data and the 3D models of the upper and/or lower dental arch. Accordingly, the 3D model of the face may ultimately be registered to the 3D models of the upper and/or lower dental arches. Additionally, the 3D model of the upper dental arch may be indirectly registered to the 3D model of the lower dental arch using the 3D model of the face and/or the intraoral scans generated during the capture of the 3D image(s) of the face. For example, since the 3D model of the upper dental arch and the 3D model of the lower dental arch are each registered to the 3D model of the face, the 3D model of the upper dental arch and the 3D model of the lower dental arch are indirectly registered to one another as well, and the position and orientation of the upper dental arch relative to the lower dental arch may be determined for the 3D model of the face.

Method 310 may be repeated one or more times during intraoral scanning. For example, as each 3D image of a face is generated, a new 3D model of the patient's face may be generated based on that 3D image (or a set of multiple 3D images generated sequentially over a brief time window). That new 3D model may be registered the 3D models of the upper and/or lower dental arches, as described above. With each 3D model of the face, the position of the lower dental arch/jaw relative to the upper dental arch/jaw may be different due to the patient moving their lower jaw and/or changing facial expressions during scanning.

FIG. 3C illustrates a flow diagram for a method 330 of combining data from face scanning and intraoral scanning, in accordance with an embodiment. At block 335 of method 330, a first intraoral scanner generates first intraoral scans of the upper and lower dental arches of a patient. At block 340, processing logic may receive the first intraoral scans and generate a 3D model of the patient's upper dental arch and a 3D model of the patient's lower dental arch using the first intraoral scans.

At block 345, the first intraoral scanner or a second intraoral scanner may optionally generate second intraoral scans of the patient's upper and/or lower dental arches (or at least portions thereof) and send the second intraoral scans to a processing device executing the processing logic.

At block 350, a face scanner generates one or more 3D images (e.g., face scan data 138A-M) of a face of the patient generated during the generation of the first intraoral scans and/or during the generation of the second intraoral scans. The intraoral scanner may be captured in the one or more 3D images of the face. In one embodiment, the first intraoral scans are generated prior to face scanning, and the 3D models of the upper and lower dental arch are generated prior to the generation of the second intraoral scans and the face scanning. In another embodiment, generation of the second intraoral scans may be omitted, and face scanning may be performed during the generation of the first intraoral scans.

At block 355, processing logic may generate a 3D model of the patient's face based on the one or more 3D images of the face. Alternatively, the 3D image(s) may themselves constitute a 3D model of the patient's face. At block 357, processing logic determines a position and/or orientation of the intraoral scanner in the 3D image(s) and/or the 3D model of the face. Such a determination of the position/orientation of the intraoral scanner may be determined based on application of one or more image processing algorithms and/or trained machine learning models to the 3D image(s) and/or the 3D model of the face.

At block 360, processing logic registers the 3D models of the upper and lower dental arch of the patient to the 3D model of the face based on at least one of a) information from the one or more 3D images (e.g., a determined position and orientation of the intraoral scanner in the 3D image(s), b) information form the first and/or second intraoral scan data (e.g., 3D surfaces in the intraoral scan data that registered to 3D surfaces in the 3D models of the upper and/or lower dental arch), or c) known position and/or orientation of the intraoral scanner to a scanned 3D surface in the intraoral scan data. Additionally, the 3D model of the upper dental arch may be indirectly registered to the 3D model of the lower dental arch using the 3D model of the face and/or the intraoral scans generated during the capture of the 3D image(s) of the face.

Method 330 may be repeated one or more times during intraoral scanning. For example, as each 3D image of a face is generated, a new 3D model of the patient's face may be generated based on that 3D image (or a set of multiple 3D images generated sequentially over a brief time window). That new 3D model may be registered the 3D models of the upper and/or lower dental arches, as described above. With each 3D model of the face, the position of the lower dental arch/jaw relative to the upper dental arch/jaw may be different due to the patient moving their lower jaw and/or changing facial expressions during scanning.

FIG. 4A illustrates a flow diagram for a method 400 of modifying a 3D model of a face, in accordance with an embodiment. The 3D model of the face may have been generated based on one or more 3D images of the face captured during intraoral scanning. Accordingly, the 3D model of the face may include a representation of the intraoral scanner, and at least some of the soft tissue of the patient's face may be distorted in the 3D model due to the insertion of the intraoral scanner's probe into the patient's mouth.

At block 405 of method 400, processing logic identifies the intraoral scanner in the 3D images of the patient's face and/or in the 3D model of the patient's face generated from the 3D images. At block 410, processing logic filters out or removes the intraoral scanner from the 3D images and/or the 3D model of the face. For example, those pixels, points of voxels identified as being part of the intraoral scanner may be removed from the 3D images and/or 3D model.

In one embodiment, at block 415 processing logic determines one or more soft tissue distortions caused by the intraoral scanner being inserted into the mouth of the patient. Such soft tissue distortions may be determined, for example, by comparison of the 3D model of the face or one or more regions of the 3D model of the face to one or more other 3D models of the face generated while no intraoral scanner was inserted into the patient's mouth and/or while the intraoral scanner was inserted into a different region of the patient's mouth. Based on such comparison, differences in positions of soft tissue and/or in relative positions between soft tissue and hard tissue may be determined between the 3D models. At block 420, processing logic modifies the 3D images and/or the 3D model of the face to remove the one or more soft tissue distortions.

FIG. 4B illustrates a flow diagram for a method 430 of generating a new model of a face at a future stage or orthodontic or prosthodontic treatment, in accordance with an embodiment. At block 435 of method 400, processing logic generates a 3D model of a face and 3D models of the upper and lower dental arches of a patient (e.g., based, respectively, on a 3D image of the face and on intraoral scans of the upper and lower dental arches). At block 440, processing logic registers the 3D model of the face to the 3D models of the upper and/or lower dental arches as described herein above. At block 445, processing logic performs treatment planning to generate 3D models of the upper and/or lower dental arches of the patient at one or more future stages of orthodontic and/or prosthodontic treatment. At block 450, processing logic generates, for one or more stage of treatment, a new 3D model of the face of the patent at that stage of treatment. The new 3D model of the face may show how a smile of the patient will look at that stage of treatment.

Figure 5A:
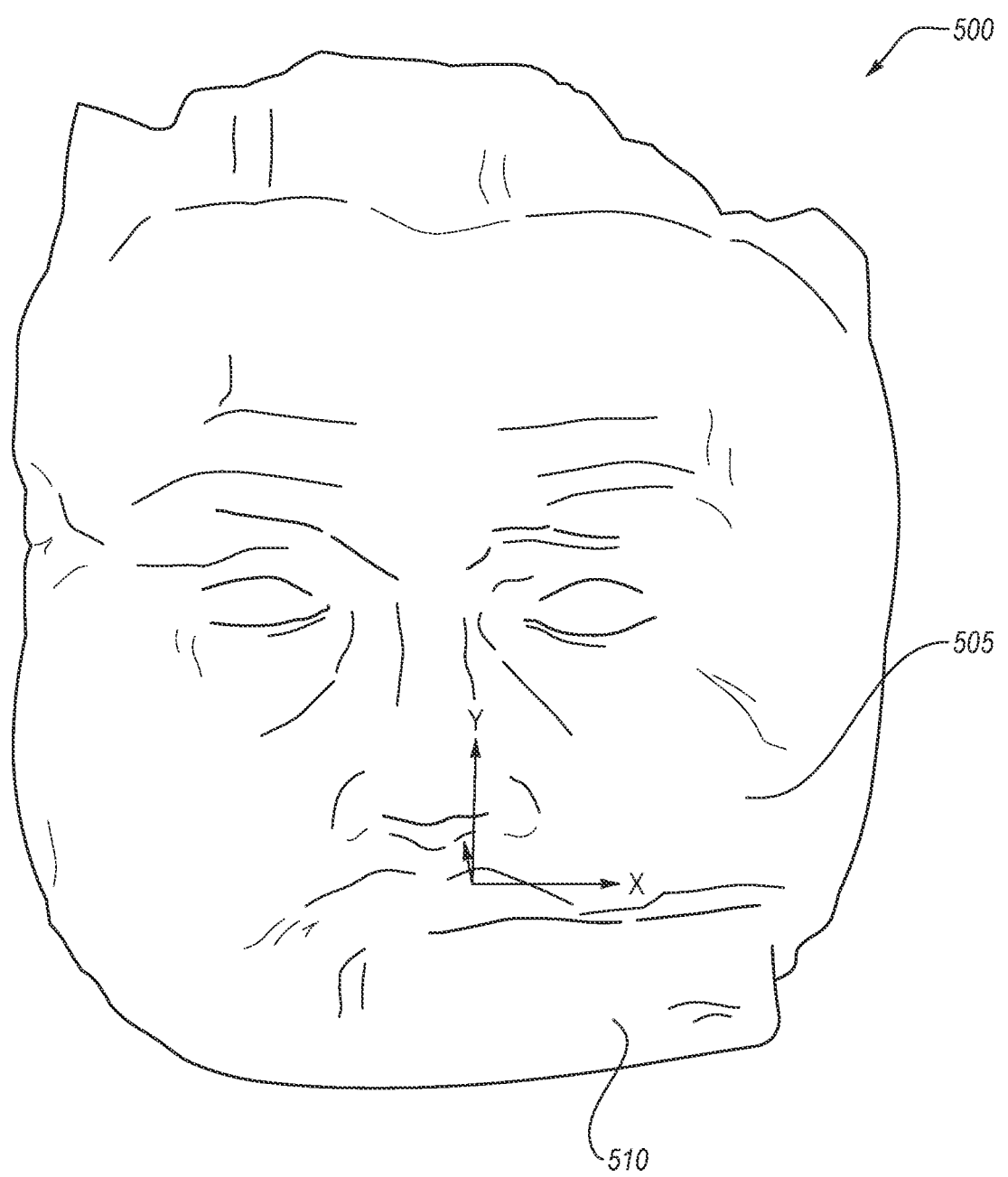
FIG. 5A illustrates a model of a patient's face and an intraoral scanner, in accordance with an embodiment.

FIG. 5A illustrates a model 500 of a patient's face 505 and an intraoral scanner 510, in accordance with an embodiment. The model 500 may have been generated based on one or more face scans captured during intraoral scanning performed by the intraoral scanner 510.

Figure 5B:
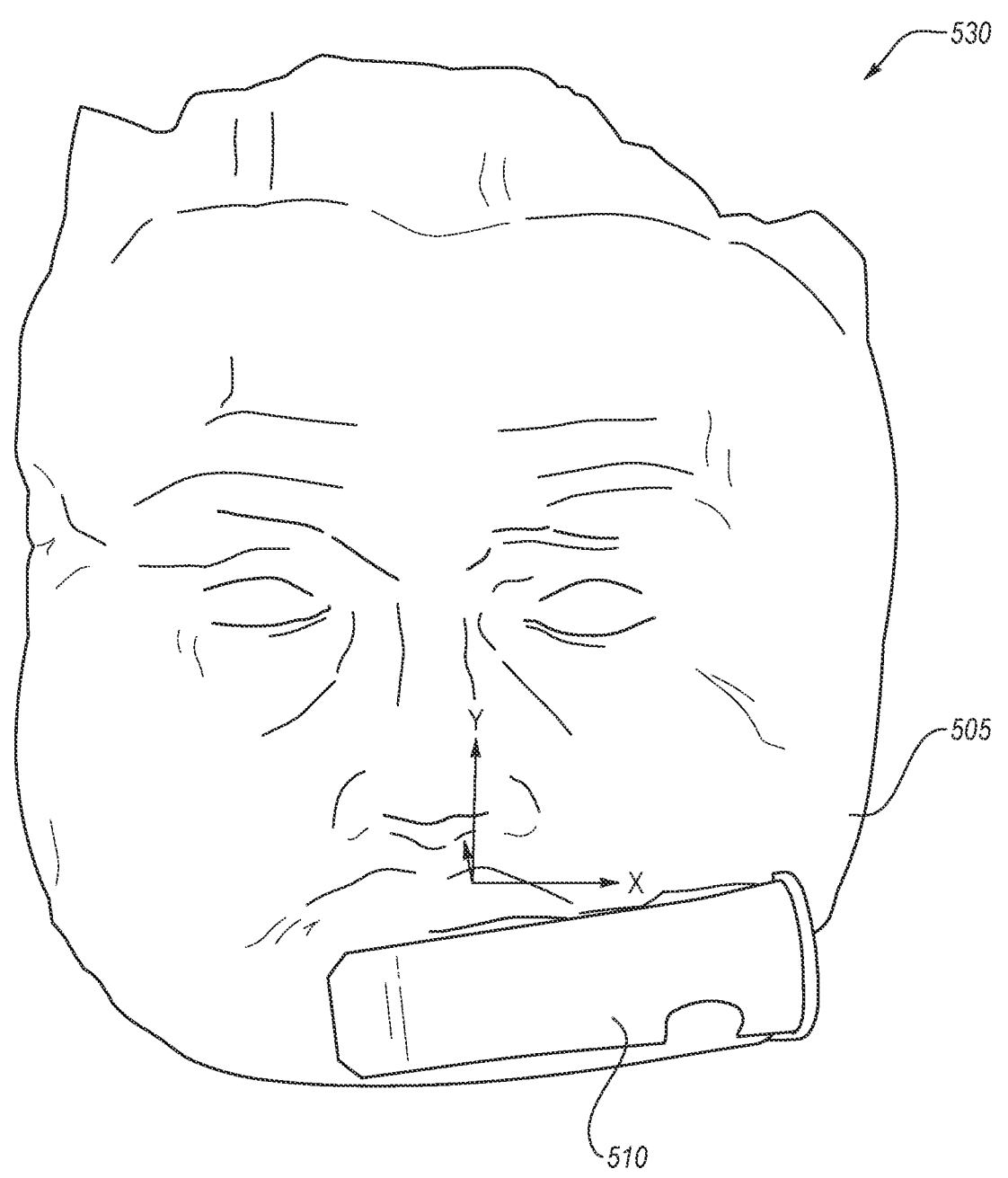
FIG. 5B illustrates the model of a patient's face and an intraoral scanner of FIG. 5A after the intraoral scanner has been identified, in accordance with an embodiment.

FIG. 5B illustrates an updated model 530 of the patient's face 505 and the intraoral scanner 510 in which the intraoral scanner 510 has been identified and labeled in the 3D model 530, in accordance with an embodiment.

Figure 5C:
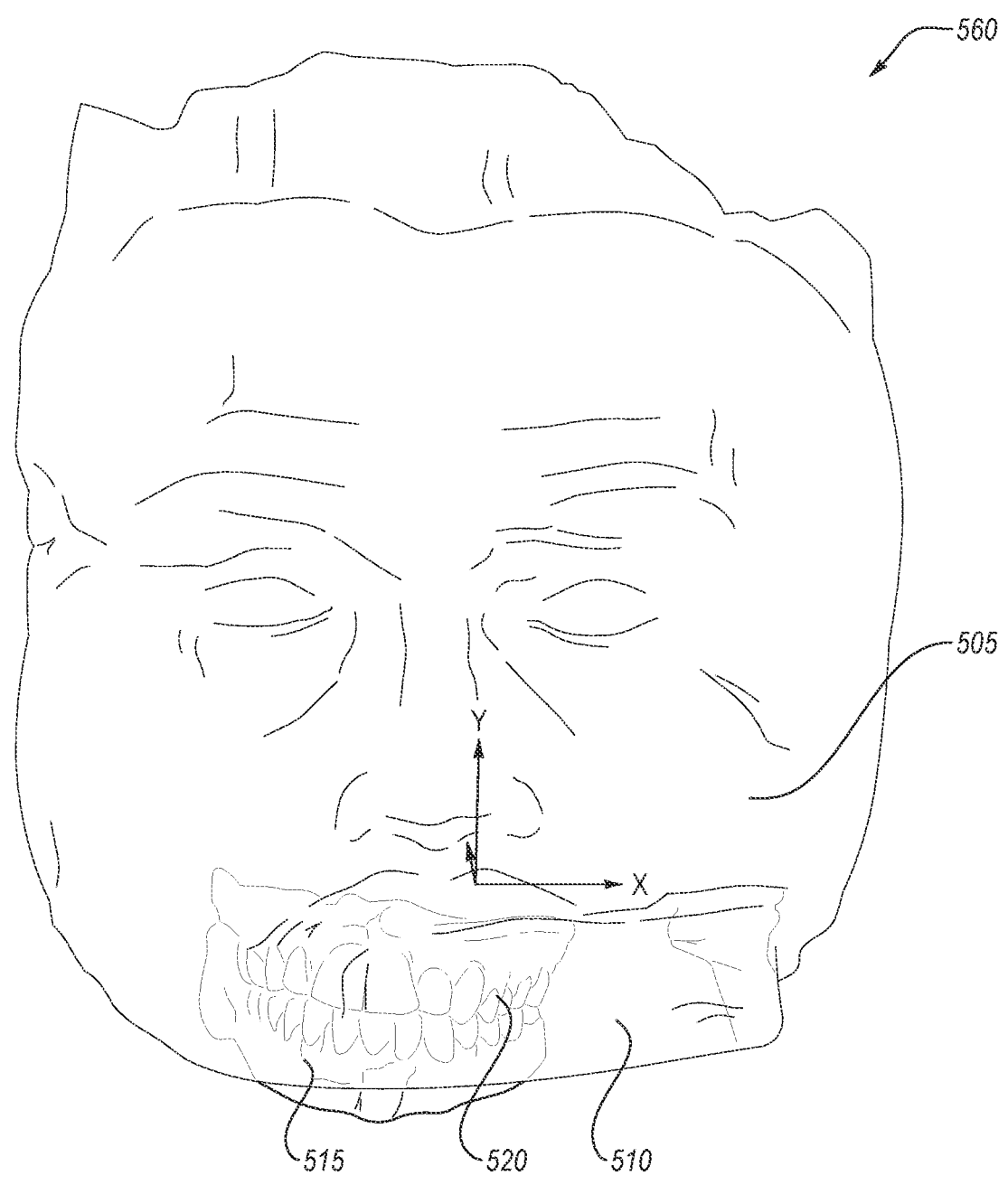
FIG. 5C illustrates the model of a patient's face and an intraoral scanner of FIG. 5A registered to 3D models of upper and lower dental arches of the patient, in accordance with an embodiment.

FIG. 5C illustrates an updated model 560 of the patient's face 505 and the intraoral scanner 510 of FIG. after a 3D model of an upper dental arch 520 and a 3D model of a lower dental arch 515 of the patient have been registered to the 3D model 560 of the face of the patient, in accordance with an embodiment.

FIG. 6 illustrates a flow diagram for a method of generating or refining a facial characteristics model relating soft tissue to hard tissue, in accordance with an embodiment. At block 610 of method 600, processing logic loads a facial characteristics model that includes a generic soft tissue mechanics function. The facial characteristics model may include multiple different generic soft tissue mechanics functions in embodiments. For example, the facial characteristics model may include different generic functions for the upper lip, the lower lip, the skin, the cheeks, the gums, ligaments, muscles, and so on. In one example, there are multiple different functions for the skin, where each function is associated with a different layer of skin.

At block 615, processing logic outputs instructions for a patient to perform a series of facial expressions. These facial expressions may be performed with and/or without an intraoral scanner inserted into the patient's mouth. At block 620, processing logic may receive a series of 3D images (or 2D images) of the face of a person or user. Each of the images in the series of images may be associated with one of the series of facial expressions. In each of the images, there may be a different relationship (e.g., different distance, different relative vertical position, different relative horizontal position, etc.) between a first set of landmarks and a second set of landmarks. These different relationships may be used at block 625 to make a determination of how the soft facial tissues respond to the series of facial expressions from the series of 3D images.

At block 630, processing logic refines the facial characteristics model based on the determination of how the soft facial tissues respond to the series of facial expressions. In one embodiment, this includes updating parameters or values in the generic soft tissue mechanics function or functions to transform these functions into one or more user specific soft tissue mechanics functions. For example, the weights associated with one or more terms of a soft tissue mechanics function may be computed or updated based on the determination made at block 625.

Figure 7:
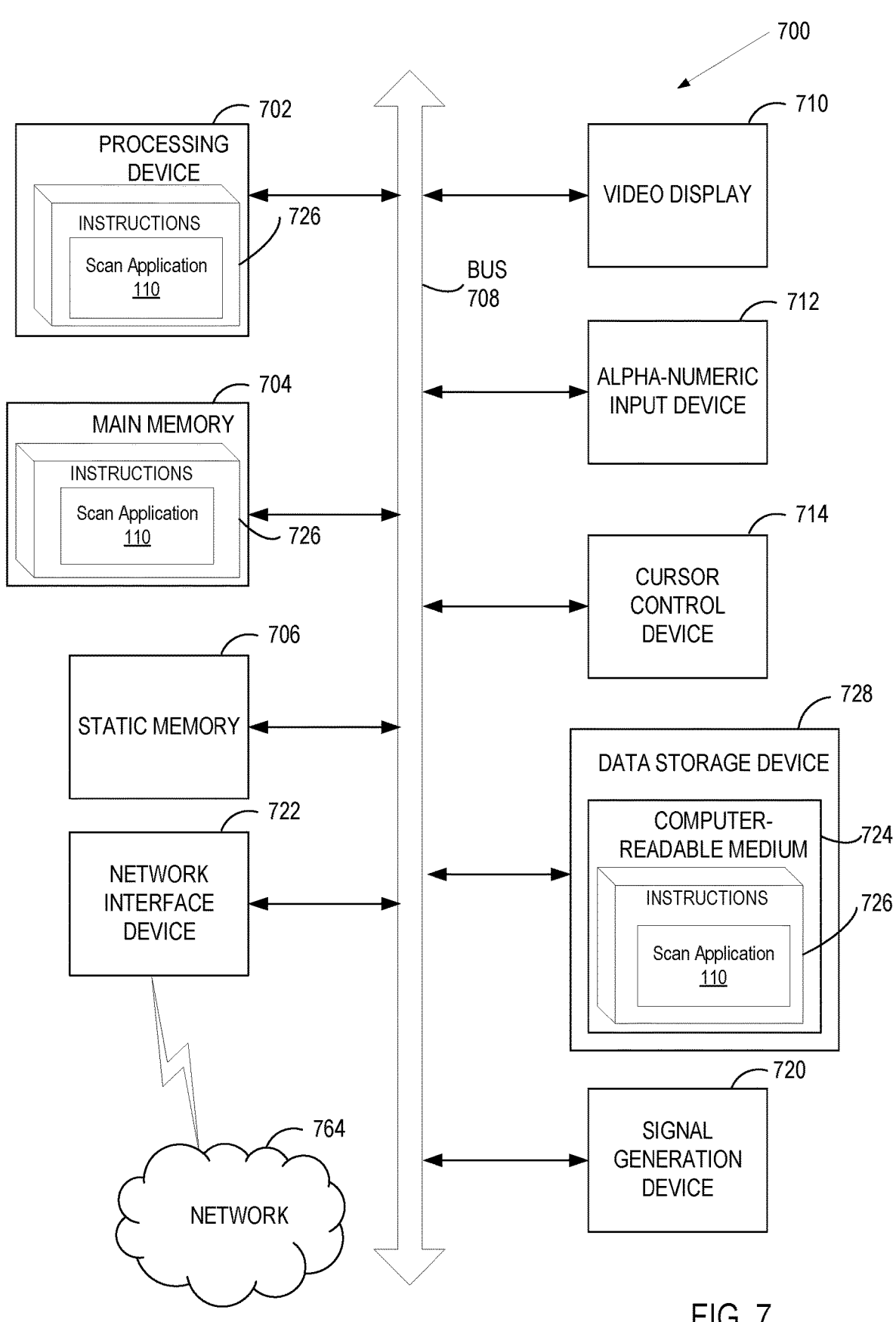
FIG. 7 illustrates a block diagram of an example computing device, in accordance with embodiments of the present disclosure.

FIG. 7 illustrates a diagrammatic representation of a machine in the example form of a computing device 700 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The computing device 700 may correspond, for example, to computing device 105 of FIG. 1. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 700 includes a processing device 702, a main memory 704 (e.g., read-only memory (ROM), flash memory, dynamic random access memory (DRAM) such as synchronous DRAM (SDRAM), etc.), a static memory 706 (e.g., flash memory, static random access memory (SRAM), etc.), and a secondary memory (e.g., a data storage device 728), which communicate with each other via a bus 708.

Processing device 702 represents one or more general-purpose processors such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. Processing device 702 is configured to execute the processing logic (instructions 726) for performing operations and steps discussed herein.

The computing device 700 may further include a network interface device 722 for communicating with a network 764. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse), and a signal generation device 720 (e.g., a speaker).

The data storage device 728 may include a machine-readable storage medium (or more specifically a non-transitory computer-readable storage medium) 724 on which is stored one or more sets of instructions 726 embodying any one or more of the methodologies or functions described herein, such as instructions for scan application 110. A non-transitory storage medium refers to a storage medium other than a carrier wave. The instructions 726 may also reside, completely or at least partially, within the main memory 704 and/or within the processing device 702 during execution thereof by the computer device 700, the main memory 704 and the processing device 702 also constituting computer-readable storage media.

The computer-readable storage medium 724 may also be used to store dental modeling logic 750, which may include one or more machine learning modules, and which may perform the operations described herein above. The computer readable storage medium 724 may also store a software library containing methods for the dental modeling logic 750. While the computer-readable storage medium 724 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media, and other non-transitory computer readable media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A system comprising:
a three-dimensional (3D) image capture device configured to capture one or more 3D images of a face of a patient;
an intraoral scanner, distinct from the 3D image capture device, comprising a plurality of features on a surface of the intraoral scanner that have a fixed position relative to one another and that enable identification of the intraoral scanner and determination of at least one of a position or an orientation of the intraoral scanner within the one or more 3D images of the face of the patient; and
a computing device operatively coupled to the intraoral scanner and to the 3D image capture device, the computing device to:
receive first intraoral scan data of a dental site of a patient generated by the intraoral scanner during intraoral scanning;
receive the one or more 3D images of the face of the patient generated by the 3D image capture device during the intraoral scanning, wherein at least some of the plurality of features of the intraoral scanner are captured in the one or more 3D images;
identify the intraoral scanner in the one or more 3D images based on the plurality of features captured in the one or more 3D images;
determine a first position of the intraoral scanner relative to the face of the patient in the one or more 3D images at least in part based on representations of the plurality of features of the intraoral scanner in the one or more 3D images; and
register the one or more 3D images of the face of the patient to the first intraoral scan data based at least in part on the first position of the intraoral scanner relative to the face of the patient in the one or more 3D images.

2. The system of claim 1, wherein the one or more 3D images of the face of the patient are registered to the first intraoral scan data based further on a known second position of the intraoral scanner relative to a 3D surface in the first intraoral scan data generated by the intraoral scanner.

3. The system of claim 2, wherein the one or more 3D images of the face of the patient are registered to the first intraoral scan data based further on a first orientation of the intraoral scanner relative to the face of the patient in the one or more 3D images and a known second orientation of the intraoral scanner relative to the 3D surface in the first intraoral scan data generated by the intraoral scanner.

4. The system of claim 1, wherein the computing device is further to:
generate a 3D model of at least one of the face of the patient or the dental site of the patient using the one or more 3D images of the face of the patient and the first intraoral scan data of the dental site of the patient.

5. The system of claim 1, wherein the computing device is further to:
receive a first 3D model of an upper dental arch of the patient and a second 3D model of a lower dental arch of the patient;
generate a third 3D model of the face of the patient based on the one or more 3D images; and
register at least one of the first 3D model of the upper dental arch or the second 3D model of the lower dental arch to the third 3D model of the face based at least in part on the first position of the intraoral scanner relative to the face of the patient in the one or more 3D images.

6. The system of claim 5, wherein the computing device is further to:
receive second intraoral scan data of the upper dental arch and third intraoral scan data of the lower dental arch;
generate the first 3D model of the upper dental arch based on the second intraoral scan data; and
generate the second 3D model of the lower dental arch based on the third intraoral scan data.

7. The system of claim 5, wherein the computing device is further to:
receive second intraoral scan data of the dental site of the patient during the intraoral scanning;
receive one or more additional 3D images of the face of the patient during the intraoral scanning, wherein the intraoral scanner is captured in the one or more additional 3D images, and wherein a position of the lower dental arch relative to the upper dental arch is different in the one or more additional 3D images than in the one or more 3D images;
generate a fourth 3D model of the face of the patient based on the one or more additional 3D images; and
register at least one of the first 3D model of the upper dental arch or the second 3D model of the lower dental arch to the fourth 3D model of the face based at least in part on a second position of the intraoral scanner relative to the face of the patient in the one or more additional 3D images.

8. The system of claim 5, wherein the computing device is further to:
filter out the intraoral scanner from at least one of the one or more 3D images of the face or the third 3D model of the face.

9. The system of claim 5, wherein the computing device is further to:
determine one or more soft tissue distortions caused by the intraoral scanner being inserted into a mouth of the patient; and
modify at least one of the one or more 3D images of the face or the third 3D model of the face to remove the one or more soft tissue distortions.

10. The system of claim 5, wherein the computing device is further to:
perform treatment planning to generate a fourth 3D model of the upper dental arch at a future stage of orthodontic or prosthodontic treatment and a fifth 3D model of the lower dental arch at the future stage of orthodontic or prosthodontic treatment; and generate a sixth 3D model of the face of the patient at the future stage of orthodontic or prosthodontic treatment showing how a smile of the patient will look at the future stage of orthodontic or prosthodontic treatment.

11. A method comprising:

receiving first intraoral scan data of a dental site of a patient during intraoral scanning by an intraoral scanner;

receiving one or more three-dimensional (3D) images of a face of the patient generated by a 3D image capture device during the intraoral scanning, wherein the intraoral scanner is captured in the one or more 3D images, and wherein the intraoral scanner comprises a plurality of features on a surface of the intraoral scanner that have a fixed position relative to one another and that enable identification of the intraoral scanner and determination of at least one of a position or an orientation of the intraoral scanner within the one or more 3D images of the face of the patient;

identifying the intraoral scanner in the one or more 3D images based on the plurality of features captured in the one or more 3D images;

determining a first position of the intraoral scanner relative to the face of the patient in the one or more 3D images at least in part based on representations of the plurality of features of the intraoral scanner in the one or more 3D images; and registering the one or more 3D images of the face of the patient to the first intraoral scan data based at least in part on the first position of the intraoral scanner relative to the face of the patient in the one or more 3D images.

12. The method of claim 11, wherein the one or more 3D images of the face of the patient are registered to the first intraoral scan data based further on a known second position of the intraoral scanner relative to a 3D surface in the first intraoral scan data generated by the intraoral scanner.

13. The method of claim 12, wherein the one or more 3D images of the face of the patient are registered to the first intraoral scan data based further on a first orientation of the intraoral scanner relative to the face of the patient in the one or more 3D images and a known second orientation of the intraoral scanner relative to the 3D surface in the first intraoral scan data generated by the intraoral scanner.

14. The method of claim 11, further comprising:

generating a 3D model of at least one of face of the patient or the dental site using the one or more 3D images of the face of the patient and the first intraoral scan data of the dental site of the patient.

15. The method of claim 11, further comprising:

receiving a first 3D model of an upper dental arch of the patient and a second 3D model of a lower dental arch of the patient;

generating a third 3D model of the face of the patient based on the one or more 3D images; and registering at least one of the first 3D model of the upper dental arch or the second 3D model of the lower dental arch to the third 3D model of the face based at least in part on the first position of the intraoral scanner relative to the face of the patient in the one or more 3D images.

16. The method of claim 15, further comprising:

receiving second intraoral scan data of the upper dental arch and third intraoral scan data of the lower dental arch;

generating the first 3D model of the upper dental arch based on the second intraoral scan data; and generating the second 3D model of the lower dental arch based on the third intraoral scan data.

17. The method of claim 15, further comprising:

receiving second intraoral scan data of the dental site of the patient during the intraoral scanning by the intraoral scanner;

receiving one or more additional 3D images of the face of the patient during the intraoral scanning, wherein the intraoral scanner is captured in the one or more additional 3D images, and wherein a position of the lower dental arch relative to the upper dental arch is different in the one or more additional 3D images than in the one or more 3D images;

generating a fourth 3D model of the face of the patient based on the one or more additional 3D images; and registering at least one of the first 3D model of the upper dental arch or the second 3D model of the lower dental arch to the fourth 3D model of the face based at least in part on a second position of the intraoral scanner relative to the face of the patient in the one or more additional 3D images.

18. The method of claim 15, further comprising:

filtering out the intraoral scanner from at least one of the one or more 3D images of the face or the third 3D model of the face.

19. The method of claim 15, further comprising:

determining one or more soft tissue distortions caused by the intraoral scanner being inserted into a mouth of the patient; and modifying at least one of the one or more 3D images of the face or the third 3D model of the face to remove the one or more soft tissue distortions.

20. The method of claim 15, further comprising:

performing treatment planning to generate a fourth 3D model of the upper dental arch at a future stage of orthodontic or prosthodontic treatment and a fifth 3D model of the lower dental arch at the future stage of orthodontic or prosthodontic treatment; and generating a sixth 3D model of the face of the patient at the future stage of orthodontic or prosthodontic treatment showing how a smile of the patient will look at the future stage of orthodontic or prosthodontic treatment.

* * * * *